(12) United States Patent
Vandegriff et al.

(10) Patent No.: US 11,359,004 B2
(45) Date of Patent: Jun. 14, 2022

(54) SUCCINIMIDE-ACTIVATED NITROXYL COMPOUNDS AND METHODS FOR THE USE THEREOF FOR NITROXYLATION OF PROTEINS

(71) Applicant: William Schindler, Santa Fe, NM (US)

(72) Inventors: Kim D. Vandegriff, Santa Fe, NM (US); Ashok Malavalli, San Diego, CA (US); Gnel Mkrtchyan, Cody, WY (US)

(73) Assignee: William Schindler, Santa Fe, NM (US)

( * ) Notice: Subject to any disclaimer, the term of this patent is extended or adjusted under 35 U.S.C. 154(b) by 0 days.

(21) Appl. No.: 16/131,487

(22) Filed: Sep. 14, 2018

(65) Prior Publication Data

US 2019/0127445 A1 May 2, 2019

Related U.S. Application Data

(62) Division of application No. 14/390,559, filed as application No. PCT/US2013/032704 on Mar. 15, 2013, now abandoned.

(60) Provisional application No. 61/619,783, filed on Apr. 3, 2012, provisional application No. 61/619,768, filed on Apr. 3, 2012.

(51) Int. Cl.
| | | |
|---|---|---|
| *C07K 14/05* | (2006.01) | |
| *C07K 14/805* | (2006.01) | |
| *C07D 403/12* | (2006.01) | |
| *C07D 401/14* | (2006.01) | |
| *C07D 401/12* | (2006.01) | |
| *A61K 38/42* | (2006.01) | |
| *C07D 207/416* | (2006.01) | |
| *C07K 14/765* | (2006.01) | |

(52) U.S. Cl.
CPC ............ *C07K 14/805* (2013.01); *A61K 38/42* (2013.01); *C07D 207/416* (2013.01); *C07D 401/12* (2013.01); *C07D 401/14* (2013.01); *C07D 403/12* (2013.01); *C07K 14/765* (2013.01)

(58) Field of Classification Search
None
See application file for complete search history.

(56) References Cited

U.S. PATENT DOCUMENTS

| | | | |
|---|---|---|---|
| 4,240,797 A | 12/1980 | Hsia | |
| 4,529,719 A | 7/1985 | Tye | |
| 4,857,636 A | 8/1989 | Hsia | |
| 5,004,809 A | 4/1991 | Bobst et al. | |
| 5,234,903 A | 8/1993 | Nho et al. | |
| 5,250,665 A | 10/1993 | Kluger et al. | |
| 5,296,465 A | 3/1994 | Rausch et al. | |
| 5,585,484 A | 12/1996 | Acharya et al. | |
| 5,591,710 A | 1/1997 | Hsia | |
| 5,650,388 A | 7/1997 | Shorr et al. | |
| 5,789,376 A | 8/1998 | Hsia | |
| 5,840,701 A * | 11/1998 | Hsia .................. | A61K 47/6445 514/9.4 |
| 6,048,967 A | 4/2000 | Hsia | |
| 6,323,175 B1 | 11/2001 | Hsia | |
| 6,458,758 B1 | 10/2002 | Hsia | |
| 6,627,738 B2 | 9/2003 | Stamler et al. | |
| 6,828,401 B2 | 12/2004 | Nho et al. | |
| 6,844,317 B2 | 1/2005 | Winslow et al. | |
| 7,005,414 B2 | 2/2006 | Barnikol et al. | |
| 7,501,499 B2 | 3/2009 | Acharya et al. | |
| 8,273,857 B2 | 9/2012 | Hsia et al. | |
| 2006/0234915 A1 | 10/2006 | Winslow | |
| 2009/0298746 A1* | 12/2009 | Acharya ................ | C07K 14/76 514/1.1 |
| 2010/0310471 A1* | 12/2010 | Kleschyov ........... | A61K 31/445 424/9.33 |
| 2010/0311657 A1 | 12/2010 | Abuchowski et al. | |
| 2011/0269709 A1 | 11/2011 | Satyam | |
| 2015/0094267 A1 | 4/2015 | Vandegriff et al. | |

FOREIGN PATENT DOCUMENTS

| | | |
|---|---|---|
| CN | 102249987 A | 11/2011 |
| WO | 91/07190 A1 | 5/1991 |
| WO | 94/09027 A1 | 4/1994 |
| WO | 95/05397 A1 | 2/1995 |

(Continued)

OTHER PUBLICATIONS

Jia eta l. (Rapid and Highly Efficient Functionalization of Polymer Bromide End-Groups by SET-NRC, Macromolecules (Washington, DC, United States) (2011), 44(7), 1747-1751).*

(Continued)

*Primary Examiner* — Maury A Audet
(74) *Attorney, Agent, or Firm* — Lewis Rice LLC

(57) ABSTRACT

The present invention relates to succinimide-activated nitroxyl compounds and methods for the synthesis of such compounds. The present invention also relates to the use of succinimide-activated nitroxyl compounds to prepare nitroxylated proteins, for example nitroxylated heme proteins (e.g., nitroxylated hemoglobin and nitroxylated myoglobin). The nitroxylated proteins are optionally also conjugated to a polyalkylene oxide (PAO), for example to a polyethylene glycol (PEG). Polynitroxylated heme proteins are useful as oxygen therapeutic agents (OTAs). The invention further relates to pharmaceutical compositions of the nitroxylated proteins and methods for the use of nitroxylated proteins in the treatment of various conditions.

18 Claims, 17 Drawing Sheets

(56) References Cited

FOREIGN PATENT DOCUMENTS

| WO | 96/29974 | A2 | | 10/1996 |
|---|---|---|---|---|
| WO | 2004/012773 | A1 | | 2/2004 |
| WO | 2004/056331 | A1 | | 7/2004 |
| WO | WO2004056331 | | * | 7/2004 |
| WO | 2006/014968 | A2 | | 2/2006 |
| WO | 2006014968 | A2 | | 2/2006 |
| WO | WO2006014968 | | * | 2/2006 |
| WO | 2009/018490 | A1 | | 2/2009 |
| WO | WO2009018490 | | * | 2/2009 |
| WO | 2011/106396 | A1 | | 9/2011 |

OTHER PUBLICATIONS

Ampulski, R. S., et al., "Determination of the Reactive Sulfhydryl Groups in Heme Proteins with 4,4'-Dipyridinedisulfide," Analytical Biochemistry, Oct. 1969, pp. 163-169, vol. 32, No. 1.
Besheer, A., et al., "Loading and Mobility of Spin-Labeled Insulin in Physiologically Responsive Complexation Hydrogels Intended for Oral Administration," Journal of Controlled Release, 2006, pp. 73-80, vol. 111, Nos. 1-2.
Blumenstein, J., et al., "Experimental Transfusion of Dextran-Hemoglobin," Blood Substitutes and Plasma Expanders, The American National Red Cross Ninth Annual Scientific Symposium, Washington, D.C., May 4-5, 1977, pp. 205-212.
Brunel, D., et al., "Grafting of Nitroxyl (TEMPO) Radical on the Surface of Silical Gel and Micelle-templated Silica (MTS)," Porous Materials in Environmentally Friendly Processes, 1999, pp. 237-244, vol. 125.
Buehler, P. W., et al., "Polynitroxyl Hemoglobin: A Pharmacokinetic Study of Covalently Bound Nitroxides to Hemoglobin Platforms," Free Radical Biology & Medicine, Jul. 2004, pp. 124-135, vol. 37, No. 1.
Degrand, C., et al., "Synthesis of Nitroxides for Use as Procationic Labels and Their Incorporation into Nation Films," The Journal of Organic Chemistry, 1993, pp. 2573-2577, vol. 58, No. 9.
Doherty, D. H., et al., "Rate of Reaction with Nitric Oxide Determines the Hypertensive Effect of Cell-Free Hemoglobin," Nature Biotechnology, Jul. 1998, pp. 672-676, vol. 16, No. 7.
Dust, J. M., et al., "Proton NMR Characterization of Poly(ethylene glycols) and Derivatives," Macromolecules, 1990, pp. 3742-3746, vol. 23, No. 16.
Eich, R. F., et al., "Mechanism of NO-Induced Oxidation of Myoglobin and Hemoglobin," Biochemistry, Jun. 1996, pp. 6976-6983, vol. 35, No. 22.
Eichler, D. C., et al., "Anti-Nitroxide Immumoglobin G: Analysis of Antibody Specificity and Their Application as Probes for Spin-Labeled Proteins," Biochemistry, Feb. 1985, p. 1181-1186, vol. 24, No. 5.
Foot, J. S., et al., "Hemoglobin bis-tetramers via Cooperative Azide-alkyne Coupling," Chemical Communications, Dec. 2009, pp. 7315-7317, No. 47.
Furchgott, R. F., "The Role of Endothelium in the Responses of Vascular Smooth Muscle to Drugs," Annual Review of Pharmacology and Toxicology, 1984, pp. 175-197, vol. 24.
Goodnough, L. T., et al., "Transfusion Medicine: Looking to the Future," The Lancet, Jan. 11, 2003, pp. 161-169, vol. 361, No. 9352.
Hess, J. R., et al., "Pulmonary and Systemic Hypertension After Hemoglobin Administration," Blood, Poster Session IV: Transfusion, Meeting Abstract 1414, 1991, pp. 356a.
Hess, J. R., et al., "Systemic and Pulmonary Hypertension After Resuscitation with Cell-Free Hemoglobin," Blood Research Division and Military Trauma Research Division, Institute Report No. 471, Jul. 1992, 37 pages.
Hoffman, M.D., et al., "Identification of Nitroxyl-induced Modifications in Human Platelet Proteins Using a Novel Mass Spectrometric Detection Method," Molecular & Cellular Proteomics, May 2009, pp. 887-903, vol. 8, No. 5.

Hsia, Carleton C.J. & Ma, Li, "A Hemoglobin-Based Multifunctional Therapeutic: Polynitroxylated Pegylated Hemoglobin", Artificial Organs, 2002, 36(2):215-220. (9 pages).
Iwashita, Y., et al., "Renal Toxicity of Hemoglobin Derivatives as Blood Substitute," Organ-Directed Toxicity: Chemical Indices and Mechanisms, Proceedings of the Symposium on Chemical Indices and Mechanisms of Organ-Directed Toxicity, 1981, pp. 97-101.
Jia, Z., "Rapid and Highly Efficient Functionalization of Polymer Bromide End-Groups by SET-NRC," Macromolecules, 2011, pp. 1747-1751, vol. 44, No. 7.
Kilbourn, R. G., et al., "Cell-Free Hemoglobin Reverses the Endotoxin-Mediated Hyporesponsivity of Rat Aortic Rings to alpha-Adrenergic Agents," Biochemical and Biophysical Research Communications, Feb. 28, 1994, pp. 155-162, vol. 199, No. 1.
Kochanek, P. M., "Novel Nitroxide Resuscitation Strategies in Experimental Traumatic Brain Injury", Pittsburgh University, Pennsylvania, Mar. 2010, Abstract Only, 1 page.
Krishna, M. C., "Studies of Structure-Activity Relationship of Nitroxide Free Radicals and Their Precursors as Modifiers Against Oxidative Damage," Journal of Medicinal Chemistry, 1998, pp. 3477-3492, vol. 41, No. 18.
Lemon, D. D., et al., "Control of the Nitric Oxide-Scavenging Activity of Hemoglobin," Biotechnology, 1996, p. 378, vol. 24.
Li, T., et al., "Structural Analysis of Heme Proteins: Implications for Design and Prediction," BMC Structural Biology, 2011, pp. 1-13, vol. 11, No. 13.
Li, W.-G., et al., "The Relationship Between Structure and Antioxidative Activity of Piperidine Nitroxides," Journal of Pharmacy and Pharmacology, Jul. 2006, pp. 941-949, vol. 58, No. 7.
MacDonald, V. W., et al., "Vasoconstrictor Effects in Isolated Rabbit Heart Perfused with Bis(3,5-Dibromosalicyl) Fumarate Cross-Linked Hemoglobin (alpha alpha Hb)," Artifical Cells, Blood Substitutes, and Immobilization Biotechnology, 1994, pp. 565-575, vol. 22, No. 3.
Muldoon, S. M., et a., "Hemoglobin-induced Contraction of Pig Pulmonary Veins," The Journal of Laboratory and Clinical Medicine, Dec. 1996, pp. 579-584, vol. 128, No. 6.
Palaparthy, R., et al., "Current Aspects in Pharmacology of Modified Hemoglobins," Advanced Drug Delivery Reviews, Feb. 2000, pp. 185-198, vol. 40, No. 3.
Patani, G. A., et al., "Bioisosterism: A Rational Approach in Drug Design," Chemical Reviews, 1996, pp. 3147-3176, vol. 96, No. 8.
Postnikova, G. B., et al., "Spin-Labelled Derivatives of Ferricytochrome C. Study of Conformational Properties and Electron Transfer in the Reaction with Oxymyoglobin," IUPAC International Symposium on Chemistry of Natural Products, Symposium Papers, 11th Edition, Sep. 17-23, 1978, pp. 87-90, vol. 1, Golden Sands, Bulgaria.
Rohlfs, R. J., et al., "Arterial Blood Pressure Responses to Cell-Free Hemoglobin Solutions and the Reaction with Nitric Oxide," The Journal of Biological Chemistry, May 1998, pp. 12128-12134, vol. 273, No. 20.
Shellington, D. K., et al., "Polynitroxylated Pegylated Hemoglobin: A Novel Neuroprotective Hemoglobin for Acute Volume-Limited Fluid Resuscitation after Combined Traumatic Brain Injury and Hemorrhagic Hypotension in Mice," Critical Care Medicine, Mar. 2011, pp. 494-505, vol. 39, No. 3.
Singh, R. J., et al., "Spin-Labeling Study of the Oxidative Damage to Low-Density Lipoprotein," Archives of Biochemistry and Biophysics, 1995, pp. 155-161, vol. 320, No. 1.
Sosnovsky, G., et al., "In the Search for new Anticancer Drugs. XXIII: Exploration of a Predictive Design for Anticancer Drugs of Carbohydrates Containing N-nitrosochloroethylamino, N-nitrosomethyl, and N-nitrosoaminoxyl Components," Journal of Pharmaceutical Sciences, 1991, pp. 693-699, vol. 80, No. 7.
Soule, B. P., et al., "The Chemistry and Biology of Nitroxide Compounds," Free Radical Biology & Medicine, 2007, pp. 1632-1650, vol. 42, No. 11.
Terwilliger, N. B., "Functional Adaptations of Oxygen-Transport Proteins," The Journal of Experimental Biology, 1998, pp. 1085-1098, vol. 201.

(56) References Cited

OTHER PUBLICATIONS

Utkin, I., et al., "Preparation and ESR Study of Spin-labeled Derivatives of Naja naja oxiana neurotoxin II.," Bioorganicheskaia khimiia, 1983, pp. 437-449, vol. 9, No. 4 (Abstract Only).

Vandegriff, K. D., et al., "Hemoglobin-Oxygen Equilibrium Curves Measured During Enzymatic Oxygen Consumption," Analytical Biochemistry, 1998, pp. 107-116, vol. 256, No. 1.

Vandegriff, K. D., et al., "Kinetics of NO and O2 Binding to a Maleimide Poly(ethylene glycol)-conjugated Human Haemoglobin," The Biochemical Journal, Aug. 2004, pp. 183-189, vol. 382, Part 1.

Vandegriff, K. D., et al., "Hemoglobin-Oxygen Equilibrium Binding: Rapid-Scanning Spectrophotometry and Singular Value Decomposition," Methods in Enzymology, 1994, pp. 460-485, vol. 232.

Winslow, R. M., "alpha alpha-Crosslinked Hemoglobin: Was Failure Predicted by Preclinical Testing?," Vox Sanguinis, 2000, pp. 1-20, vol. 79, No. 1.

Winslow, R. M., et al., "Oxygen Equilibrium Curve of Normal Human Blood and Its Evaluation by Adair's Equation," The Journal of Biological Chemistry, 1977, pp. 2331-2337, vol. 252.

Winslow, R. M., et al., "Vascular Resistance and the Efficacy of Red Cell Substitutes in a Rat Hemorrhage Model," Journal of Applied Physiology, Sep. 1998, pp. 993-1003, vol. 85, No. 3.

Wu, X., et al., "Polynitroxylated Pegylated Hb (PNPH) in Resuscitation of Traumatic Brain Injury + Hemorrhagic Shock", 2009 Annual Meeting of the American Society Anesthesiologists, Abstract Only, 2 pages.

Yang, Y., et al., "Efficient CuAAC Click Information of Functional Hemoglobin bis-tetramers," Chemical Communications, 2010, pp. 7557-7559, vol. 46, No. 40.

Zalipsky, S., et al., "Attachment of Drugs to Polyethylene Glycols," European Polymer Journal, 1983, pp. 1177-1183, vol. 19, No. 12.

\* cited by examiner

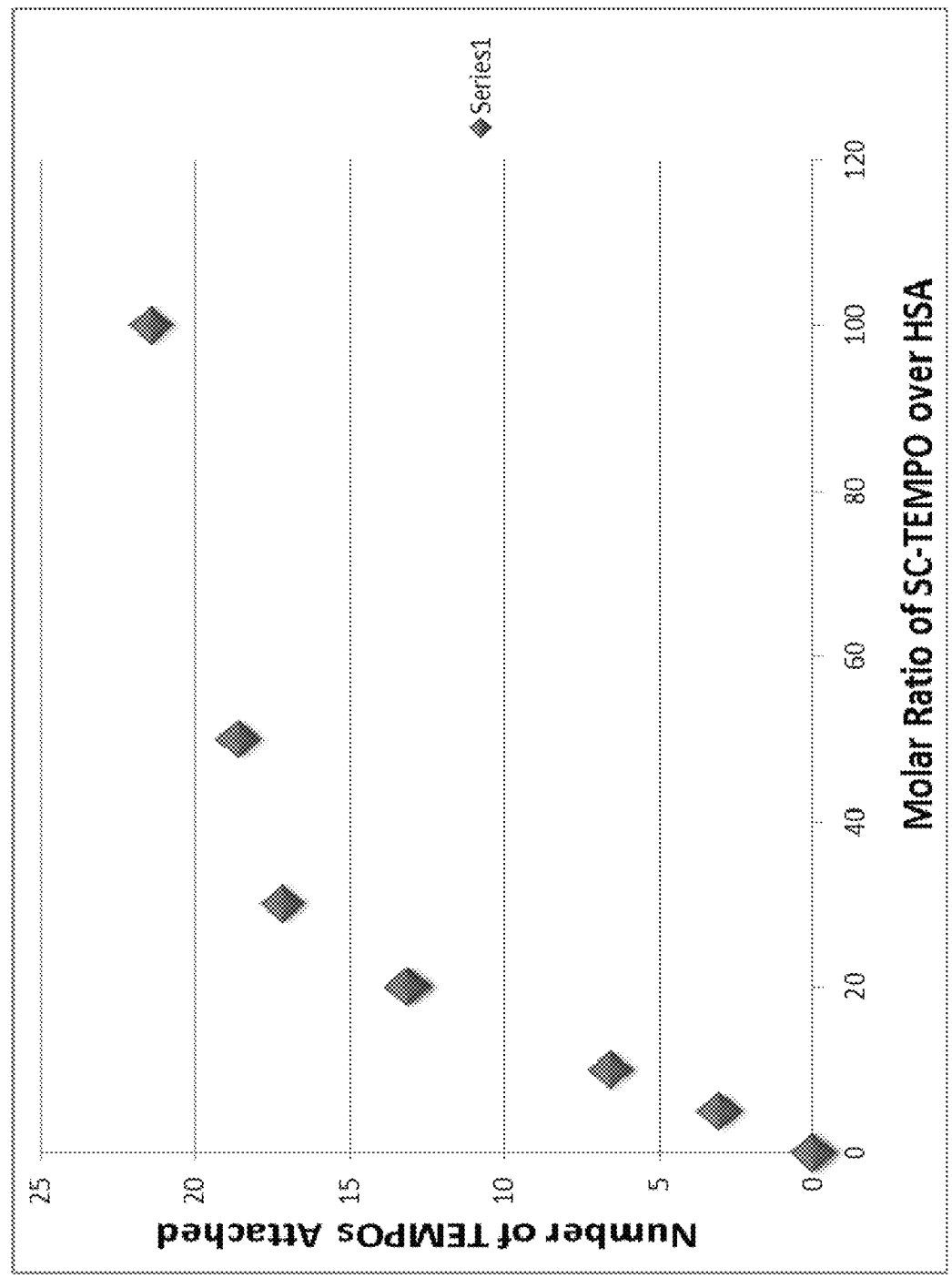
FIG. 17  Reaction Kinetics: Number of conjugated TEMPO based on MALDI-TOF Analysis

SUCCINIMIDE-ACTIVATED NITROXYL COMPOUNDS AND METHODS FOR THE USE THEREOF FOR NITROXYLATION OF PROTEINS

REFERENCE TO RELATED APPLICATIONS

This application is a continuation of U.S. patent application Ser. No. 14/390,559, filed Oct. 3, 2014, which is a U.S. national stage application of International Patent Application No. PCT/US2013/032704, filed Mar. 15, 2013, which claims the benefit of U.S. Provisional Patent Application Ser. No. 61/619,783, filed Apr. 3, 2012, and U.S. Provisional Patent Application Ser. No. 61/619,768, filed Apr. 3, 2012. Each of the above-cited applications is incorporated by reference herein in its entirety.

FIELD OF THE INVENTION

The present invention generally relates to succinimide-activated nitroxyl compounds and methods for the synthesis of succinimide-activated nitroxyl compounds. The present invention also relates to the use of succinimide-activated nitroxyl compounds to prepare nitroxylated proteins, for example nitroxylated heme proteins (e.g., nitroxylated hemoglobin and nitroxylated myoglobin). The nitroxylated proteins are optionally also conjugated to a polyalkylene oxide (PAO), for example to a polyethylene glycol (PEG). Polynitroxylated heme proteins are useful as oxygen therapeutic agents (OTAs) and are capable of delivering molecular oxygen, carbon monoxide, nitric oxide and mixtures thereof. Thus, the invention further includes pharmaceutical compositions of the nitroxylated proteins and methods for the use of nitroxylated proteins in the treatment of various conditions.

BACKGROUND OF THE INVENTION

Hemoglobin-based oxygen carriers ("HBOC") have long been associated with vasoconstriction that has been attributed to nitric oxide (NO) scavenging by heme. Oxygen carriers that are useful as oxygen therapeutics (sometimes referred to as "oxygen-carrying plasma expanders"), such as stabilized hemoglobin (Hb), have been shown to have limited efficacy because they scavenge nitric oxide, causing vasoconstriction and hypertension. The propensity of these oxygen carrying solutions to cause vasoconstriction can manifest as hypertension in animals and man. Although the mechanisms underlying the vasoconstrictive effects of HBOCs are not well understood, it has been suggested that the heme iron may combine rapidly and irreversibly with endogenous NO, a powerful vasodilator, thereby causing vasoconstriction.

In part because of these vasoconstrictive effects, no oxygen carrier to date has been entirely successful as an oxygen therapeutic agent (OTA), although products comprising modified cell-free Hb have been the most promising. Human Hb cross-linked between α-chains with bis-dibromosalicylfumarate (ααHb) was developed by the U.S. Army as a model red cell substitute, but was abandoned after it exhibited severe increases in pulmonary and systemic vascular resistance (Hess, J. et al., 1991, Blood 78:356A). A commercial version of this product was also abandoned after a disappointing Phase III clinical trial (Winslow, R. M., 2000, Vox Sang 79:1-20).

Two molecular approaches have been advanced in attempting to overcome the NO binding activity of Hb. The first approach used site-directed mutagenesis of the distal heme pocket in an attempt to create a recombinant hemoglobin with reduced NO-binding affinity (Eich, R. F. et al., 1996, Biochem. 35:6976-83). The second approach used a chemical modification approach wherein the size of the Hb was enhanced through oligomerization in an attempt to reduce or possibly completely inhibit the extravasation of Hb from the vascular space into the interstitial space (Hess, J. R. et al., 1978, J. Appl. Physiol. 74:1769-78; Muldoon, S. M. et al., 1996, J. Lab. Clin. Med. 128:579-83; Macdonald, V. W. et. al., 1994, Biotechnology 22:565-75; Furchgott, R., 1984, Ann. Rev. Pharmacol. 24:175-97; and Kilbourne, R. et al., 1994, Biochem. Biophys. Res. Commun. 199:155-62).

In fact, recombinant Hbs with reduced association binding rates for NO have been produced that are less hypertensive in top-load rat experiments (Doherty, D. H. etg al. 1998, Nature Biotechnology 16:672-676 and Lemon, D. D. et al. 1996, Biotech 24:378). However, studies suggest that NO binding may not be the only explanation for the vasoactivity of Hb. It has been found that certain large Hb molecules, such as those modified with polyethylene glycol (PEG), were virtually free of vasoconstriction, even though their NO association rates were identical to those of the severely hypertensive ααHb (Rohlfs, R. J. et al.1998, J Biol. Chem. 273:12128-12134). Furthermore, it was found that PEG-Hb was extraordinarily effective in preventing the consequences of hemorrhage when given as an exchange transfusion prior to hemorrhage (Winslow, R. M. et al. 1998, J. Appl. Physiol. 85:993-1003).

The conjugation of PEG to Hb reduces its antigenicity and extends its circulation half-life. However, the PEG conjugation reaction has been reported to result in dissociation of Hb tetramers into αβ-dimer subunits causing gross hemoglobinuria in exchange-transfused rats receiving PEG-conjugates of Hb monomeric units below 40,000 Daltons ("Da") (Iwashita and Ajisaka Organ-Directed Toxicity: Chem. Indicies Mech., Proc. Symp., Brown et al. 1981, Eds. Pergamon, Oxford, England pgs 97-101). A polyalkylene oxide ("PAO") conjugated Hb having a molecular weight greater than 84,000 Daltons was prepared by Enzon, Inc. (U.S. Pat. No. 5,650,388) that carried about 10 copies of PEG-5,000 chains linked to Hb at its α and ε-amino groups. This degree of substitution was described as avoiding clinically significant nephrotoxicity associated with hemoglobinuria in mammals. However, the conjugation reaction resulted in a heterogeneous conjugate population and contained other undesirable reactants that had to be removed by column chromatography.

PEG conjugation is typically carried out through the reaction of an activated PEG moiety with a functional group on the surface of biomolecules. The most common functional groups are the amino groups of lysine, imidazole groups of histidine residues, and the N-terminus of proteins; thiol groups of cysteine residues; and the hydroxyl groups of serine, threonine and tyrosine residues and the C-terminus of the protein. PEG is usually activated by converting the hydroxyl terminus to a reactive moiety capable of reacting with these functional groups in a mild aqueous environment. One of the most common monofunctional PEGs used for conjugation of therapeutic biopharmaceuticals is methoxy-PEG ("mPEG-OH"), which has only one functional group (i.e. hydroxyl), thus minimizing cross-linking and aggregation problems that are associated with bifunctional PEG. However, mPEG-OH is often contaminated with high molecular weight bifunctional PEG (i.e. "PEG diol"), which can range as high as 10 to 15% (Dust J. M. et al. 1990, Macromolecule 23:3742-3746) due to its production process. This bifunctional PEG diol has roughly twice the size of the desired monofunctional PEG. The contamination problem is further aggravated as the molecular weight of PEG increases. The purity of mPEG-OH is especially critical for the production of PEGylated biotherapeutics, because the FDA requires a high level of reproducibility in the production processes and quality of the final drug product.

Conjugation of Hb to PAOs has been performed in both the oxygenated and deoxygenated states. U.S. Pat. No. 6,844,317 describes conjugating Hb in the oxygenated, or "R" state by equilibrating Hb with the atmosphere prior to conjugation to enhance the oxygen affinity of the resultant PEG-Hb conjugate. Others describe a deoxygenation step prior to conjugation to diminish the oxygen affinity and increase structural stability, enabling the Hb to withstand the physical stresses of chemical modification, diafiltration and/or sterile filtration and pasteurization (U.S. Pat. No. 5,234,903). For intramolecular cross-linking of Hb, it is suggested that deoxygenating Hb prior to modification may be required to expose lysine 99 of the α-chain to the cross-linking reagent (U.S. Pat. No. 5,234,903).

The kinetics of Hb thiolation with 2-iminothiolane prior to conjugation with PEG was investigated by Acharya et al. (U.S. Pat. No. 7,501,499). It was observed that increasing the concentration of iminothiolane from 10-fold, which introduced an average of five extrinsic thiols per tetramer, to 30-fold nearly doubled the number of extrinsic thiols on Hb. However, the size enhancement seen after PEG conjugation was only marginal, even with double the number of thiols. This suggested that the conjugation reaction in the presence of 20-fold molar excess of maleimidyl PEG-5000 covered the surface of the Hb with less reactive thiols, resulting in steric interference that resisted further modification of Hb with more reactive thiols. Consequently, to achieve the desired degree of conjugation of modified Hb (i.e. 6±1 PEG per Hb molecule), Acharya et al. thiolated Hb with an 8-15 molar excess of iminothiolane, and then reacted the thiolated Hb with a 16-30 fold molar excess of maleimidyl PEG-5000. However, these high molar excess reactant concentrations in large-scale production significantly increase the cost for preparing the HBOC and increase the heterogeneity of the final product. Moreover, such high molar excess of the maleimidyl PEG-5000 also results in a more heterogeneous product with the production of a greater number of unwanted side reactants.

In previous studies, it was observed that the molecular size of surface modified hemoglobin has to be large enough to avoid being cleared by the kidneys and to achieve the desired circulation half-life. Blumenstein, J. et al., determined that this could be achieved at, or above, a molecular weight of 84,000 Daltons ("Da") ("Blood Substitutes and Plasma Expanders," Alan R. Liss, editors, New York, N.Y., pages 205-212 (1978)). In that study, the authors conjugated dextran of varying molecular weight to Hb. They reported that a conjugate of Hb (with a molecular weight of 64,000 Da) and dextran (having a molecular weight of 20,000 Da) "was cleared slowly from the circulation and negligibly through the kidneys." Further, it was observed that increasing the molecular weight above 84,000 Da did not significantly alter these clearance curves. Intramolecular cross-linking chemically binds together subunits of the tetrameric hemoglobin unit to prevent the formation of dimers which are prematurely excreted by the kidney. (See, e.g., U.S. Pat. No. 5,296,465)

Nitroxides are well-established antioxidant compounds of low toxicity that attenuate oxidative damage in animal models of inflammatory disease and preserve bioavailable NO gas. They are believed to exert protective effects principally by acting as SOD mimetics or radical scavengers. Thus, polynitroxylated compounds have antioxidant and anti-inflammatory properties. This is not to be confused with combining HBOCs with nitric oxide (NO) donor molecules, which have been reported to enhance vascular relaxation. See, e.g., U.S. Patent Application Publication No. 2010/0311657. However, SOD-mimetic nitroxides have a short plasma half-life due to their small size, and thus it is difficult to maintain the antioxidant efficacy of these molecules in vivo.

In view of the foregoing, there is a need in the art for oxygen therapeutic agents that do not cause vasoconstriction and hypertension and that have antioxidant and anti-inflammatory properties.

Moreover, current methods for activating nitroxides for use as nitroxylating agents are multistep and expensive processes. There is therefore a need in the art for methods for simple and inexpensive methods for making activated nitroxide compounds for use as nitroxylating agents.

SUMMARY OF THE INVENTION

One aspect of the present invention relates to a nitroxylating agent of formula (I):

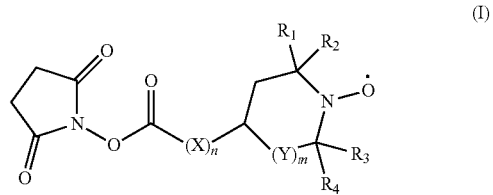

wherein each of $R_1$, $R_2$, $R_3$, and $R_4$ is independently $C_1$-$C_4$ alkyl; X is oxygen, sulfur, nitrogen, phosphorus, or silicon; Y is $CH_2$; n is 0 or 1; and m is 0 or 1.

Another aspect of the invention relates to a method for preparing a nitroxylating agent of the formula (II):

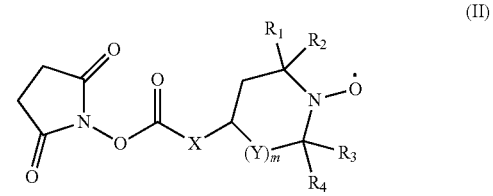

comprising reacting a compound having the formula (III)

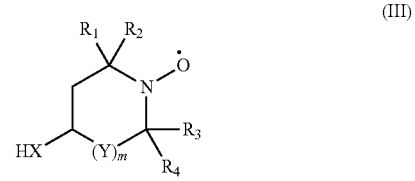

with N,N'-disuccinimidyl carbonate (DSC) in the presence of an organic base; wherein each of $R_1$, $R_2$, $R_3$, and $R_4$ is independently $C_1$-$C_4$ alkyl; X is oxygen, sulfur, nitrogen, phosphorus, or silicon; Y is $CH_2$; and m is 0 or 1.

Yet another aspect of the invention is also directed to a method for preparing a nitroxylating agent of the formula (IV):

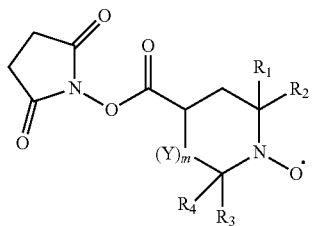
(IV)

comprising reacting a compound having the formula (V)

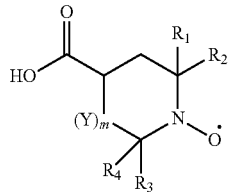
(V)

with N-hydroxysuccinimide (NHS) in the presence of N,N'-dicyclohexylcarbodiimide (DCC); wherein each of $R_1$, $R_2$, $R_3$, and $R_4$ is independently $C_1$-$C_4$ alkyl; Y is $CH_2$; and m is 0 or 1.

A further aspect is a nitroxylated protein comprising at least one nitroxylated amino group and the nitroxylated protein can have the structure (VI):

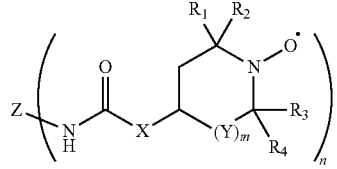
(VI)

wherein Z represents the protein; each of $R_1$, $R_2$, $R_3$, and $R_4$ are independently $C_1$-$C_4$ alkyl; X is oxygen, sulfur, nitrogen, phosphorus, or silicon; Y is $CH_2$; m is 0 or 1; n is the average number of activated-PEG polymers conjugated to the protein, the —NH-group is an amine group of the protein and N is a nitrogen of the protein.

Yet another aspect or the invention is a nitroxylated protein that can comprise at least one nitroxylated amino group, the nitroxylated protein having the structure (VII):

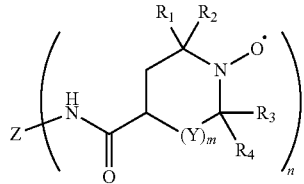
(VII)

wherein Z represents the protein; each of $R_1$, $R_2$, $R_3$, and $R_4$ are independently $C_1$-$C_4$ alkyl; Y is $CH_2$; m is 0 or 1; n is the average number of activated-PEG polymers conjugated to the protein; the —NH-group is an amine group of the protein; and N is a nitrogen of the protein.

Another aspect is a nitroxylated protein having a conjugated PEG that is a maleimide-PEG, wherein the maleimide-PEG conjugated to an intrinsic thiol moiety of a cysteine residue or conjugated to a thiol moiety of a thiolated lysine residue has the structure (VIII)

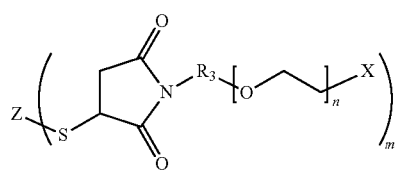
(VIII)

wherein Z represents the protein, S is the thiol group of the protein, $R_3$ is an alkylene or phenylene group, X is a terminal group, m is the average number of activated-PEG polymers conjugated to the protein, and n represents the average number of oxyethylene units of a PEG having an average molecular weight of about 2,000 to about 20,000 Daltons.

A further aspect is a nitroxylated protein having a conjugated PEG that is a maleimide-PEG, wherein the maleimide-PEG conjugated to an intrinsic thiol moiety of a cysteine residue or conjugated to a thiol moiety of a thiolated lysine residue has the structure (VIII)

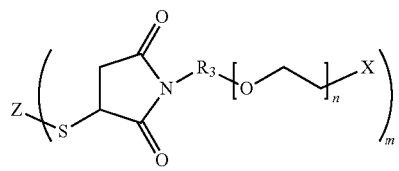
(VIII)

wherein Z represents the protein, S is the thiol group of the protein, $R_3$ is an alkylene or phenylene group, X is a terminal group, m is the average number of activated-PEG polymers conjugated to the protein, and n represents the average number of oxyethylene units of a PEG having an average molecular weight of about 2,000 to about 20,000 Daltons.

Another aspect of the invention is a method for preparing a nitroxylated protein comprising reacting the protein with a nitroxylating agent of formula (IV):

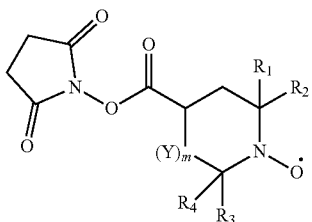
(IV)

wherein each of $R_1$, $R_2$, $R_3$, and $R_4$ is independently $C_1$-$C_4$ alkyl; Y is $CH_2$; and m is 0 or 1. method of claim G2, wherein each of $R_1$, $R_2$, $R_3$, and $R_4$ is independently —$CH_3$.

A further aspect is a method for making a nitroxylated protein using the nitroxylating agent of formula (II) or (IV) wherein the maleimide-PEG conjugated to an intrinsic thiol moiety of a cysteine residue has the structure (VIII)

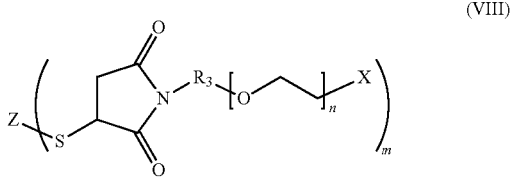

(VIII)

wherein Z represents the protein, $R_3$ is an alkylene or phenylene group, S is the thiol group of the protein, m is the average number of activated-PEG polymers conjugated to the protein, and n represents the average number of oxyethylene units of a PEG having an average molecular weight of about 2,000 to about 20,000 Daltons.

BRIEF DESCRIPTION OF THE DRAWINGS

FIG. 17 shows representative results of an experiment wherein HSA was nitroxylated using 4-Succinimidyl-TEMPO-Carbonate (4-STC) at a molar excess of 1:5-1:100 over HSA.

DEFINITIONS

Figure 1:
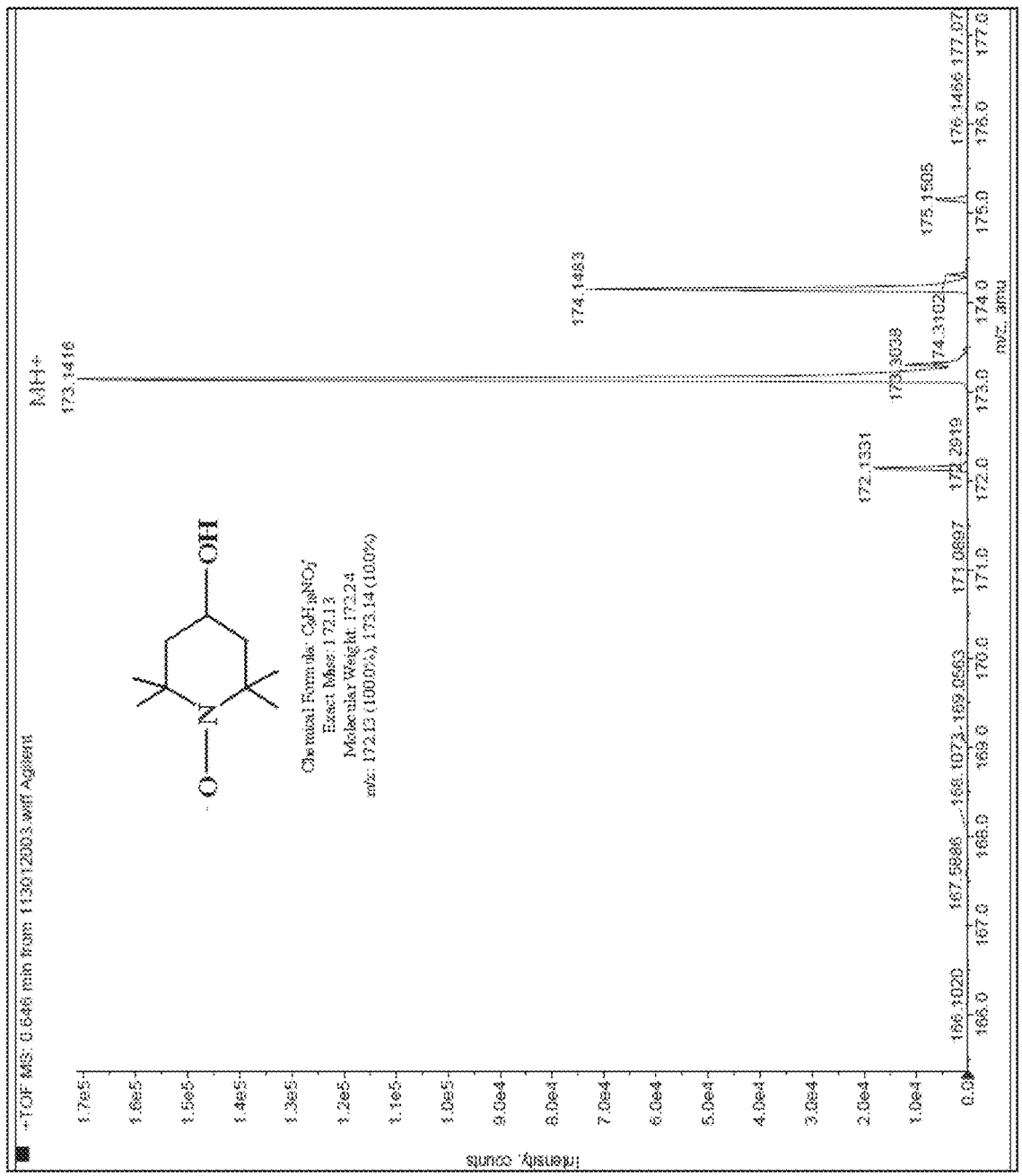
FIG. 1 shows the results of ESI-TOF high accuracy mass spectroscopy of 4-hydroxy-2,2,6,6-tetramethylpiperidin-1-oxyl (TEMPOL).

When the terms "one," "a" or "an" are used in this disclosure, they mean "at least one" or "one or more," unless otherwise indicated.

"Activated polyalkylene oxide" or "activated PAO" as used herein refer to a PAO molecule that has at least one functional group. A functional group is a reactive moiety that interacts with free amines, sulfhydryls or carboxyl groups on a molecule to be conjugated with PAO. For example, one such functional group that reacts with free sulfhydryls is a maleimide group. A functional group that reacts with free amines is a succinimide group.

"Deoxyhemoglobin" or "unliganded hemoglobin" means any hemoglobin to which no exogenous ligand is bound to heme.

"Hemoglobin" or "Hb" refers generally to a heme protein that transports oxygen. In humans, each molecule of Hb has 4 subunits, 2 α-chain subunits and 2 β-chain subunits, which are arranged in a tetrameric structure. Each subunit also contains one heme group, which is the iron-containing center that in the ferrous ($Fe^{2+}$) binds the ligands $O_2$, NO or CO. Thus, each Hb molecule can bind up to 4 ligand molecules, making $HbO_2$, HbNO, or HbCO liganded compounds, respectively. Additionally, the hemoglobin may be liganded with mixtures of $O_2$, NO and CO.

"Hemoglobin based oxygen carriers" (HBOCs) refers to hemoglobins that carry oxygen, but are also useful for carrying other molecular gases, such as carbon monoxide and nitric oxide.

"High oxygen affinity" refers to hemoglobin that has been modified to exhibit an oxygen affinity greater than that of stroma free-hemoglobin (SFH). Thus, a "high oxygen affinity" Hb has a P50 less than that of SFH, which has a P50 of 15 mmHg as measured at 37° C. and pH 7.4.

"Liganded hemoglobin" means hemoglobin to which an exogenous ligand is bound to heme. Common preferred ligands include oxygen, carbon monoxide, and nitric oxide.

"MalPEG" refers to maleimidyl polyethylene glycol, and includes a maleimidyl moiety attached to polyethylene glycol via a linker.

"MalPEG-Hb" refers to Hb to which maleimidyl-activated PEG has been conjugated. The conjugation is performed by reacting MalPEG with thiol groups (and to a lesser extent, amino groups) on the Hb to form MalPEG-Hb. Thiol groups are found in cysteine residues present in the amino acid sequence of Hb, such as the two intrinsic thiols at βCys 93, and can also be introduced by modifying surface amino groups to contain a thiol group. An exemplary MalPEG-Hb known as MP4 (Sangart, Inc.) has the following formula:

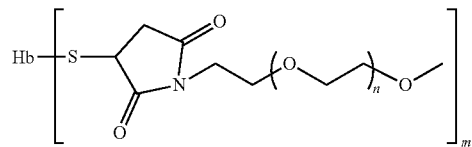

wherein Hb is hemoglobin; S is a thiol group on the hemoglobin; n is the number of oxyethylene units of the 5,000-Dalton polyalkylene oxide polymer; and m is the average number of maleimidyl-activated polyalkylene oxide polymers conjugated to the hemoglobin and is 7-8.

"Methemoglobin" or "metHb" refer to an oxidized form of Hb that contains iron in the ferric state. MetHb does not function as an oxygen or CO carrier. The term "methemoglobin %" as used herein refers to the percentage of oxidized Hb to total Hb.

"Methoxy-PEG" or "mPEG-OH" refer to PEG wherein the hydrogen of the hydroxyl terminus is replaced with a methyl (—$CH_3$) group.

"Modified hemoglobin" or "modified Hb" refers to Hb that has been altered by a chemical reaction, such as intraand inter-molecular crosslinking, polymerization, conjugation, and/or recombinant techniques, such that the Hb is no longer in its "native" state. As used herein, the terms "hemoglobin" or "Hb" refer to both native unmodified Hb and modified Hb, unless otherwise indicated.

"Nitrite reductase activity" or "NRA" is the ability of hemoglobin or a hemoglobin-based protein to reduce nitrite to nitric oxide. "Maximal nitrite reductase activity" is the maximum rate that hemoglobin or a hemoglobin-based protein is able to reduce nitrite to nitric oxide. "Initial nitrite reductase activity" is the initial rate that hemoglobin or a hemoglobin-based protein reduces nitrite to nitric oxide when nitrite is added to the fully deoxygenated protein.

The term "non-oxygenated" means that the heme protein or hemoglobin is in the non-liganded, deoxygenated state, or it is liganded with a gas other than $O_2$, such as NO or CO.

"Oxygen affinity" refers to the avidity with which an oxygen carrier, such as Hb, binds molecular oxygen. This characteristic is defined by the oxygen equilibrium curve, which relates the degree of saturation of Hb molecules with oxygen (Y axis) with the partial pressure of oxygen (X axis). The position of this curve is denoted by the "$P_{50}$" value, which is the partial pressure of oxygen at which the oxygen carrier is half-saturated with oxygen, and is inversely related to oxygen affinity. Hence, the lower the $P_{50}$, the higher the oxygen affinity. The oxygen affinity of whole blood (and components of whole blood, such as red blood cells and Hb) can be measured by a variety of methods known in the art. (see, e.g., Winslow, R. M. et al., J. Biol. Chem. 1977, 252:2331-37). Oxygen affinity may also be determined using a commercially available HEMOX™ Analyzer (TCS Scientific Corporation, New Hope, Pa.). (see, e.g., Vandegriff and Shrager in "Methods in Enzymology" (Everse et al., eds.) 232:460 (1994)); and Vandegriff, et al., Anal. Biochem. 256(1): 107-116 (1998)).

The term "oxygen therapeutic agent" as used herein refers to a heme protein that is capable of binding to and carrying molecular oxygen to cells/tissues/organs in need thereof. When administered in the form of a CO- or NO-liganded heme protein, once the CO or NO is released from the heme moiety, the heme groups are then free to bind to and carry molecular oxygen.

"Polyethylene glycol" or "PEG" refer to a polymer of the general chemical formula $H(OCH_2CH_2)_n$ OH where "n" is greater than or equal to 4, preferably about 45 to about 500, more preferably about 70 to about 250, and most preferably about 90 to about 140, or about 115. The polymer can be substituted or unsubstituted, and the terminal hydroxy group can be replaced with a different conventional terminal group, such as methoxy or carboxy. PEGs are commercially available from many sources (e.g., Carbowax™ (Dow Chemical, Midland, Mich.), Poly-G® (Arch Chemicals, Norwalk, Conn.) and Solbase).

"Polyethylene glycol-conjugated hemoglobin," "PEG-Hb conjugate" or "PEG-Hb" refer to Hb to which at least one PEG is covalently attached.

"Solution" refers to a liquid mixture and the term "aqueous solution" refers to a solution that contains some water and may also contain one or more other liquid substances with water to form a multi-component solution.

"Stroma-free hemoglobin" or "SFH" refer to Hb from which red blood cell membranes have been removed.

"Surface-modified hemoglobin" refers to hemoglobin to which chemical groups, usually polymers, have been attached, such as dextran or polyalkylene oxide. The term "surface-modified oxygenated hemoglobin" refers to Hb that is in the "R" state when it is surface modified.

"Terminal activity" is an indication of the percentage of PAO that is functionalized with a moiety capable of reacting with a reactive group of the heme protein or hemoglobin. "100% Terminal activity" indicates that the molar excess of the PAO used in the conjugation reaction is expressed on a basis that all of the PAO has a moiety capable of reacting with a reactive group of the heme protein or hemoglobin. For example, if an available Mal-PEG has 80% terminal activity such that 80% of the PEGs are functionalized with Mal, and the Mal-PEG is used in 20-fold molar excess over hemoglobin, then this molar ratio can be expressed as a 16-fold molar excess of Mal-PEG over hemoglobin based on 100% terminal activity.

"Thiolation" refers to a process that increases the number of sulfhydryl groups on a molecule. For example, reacting a protein with 2-iminothiolane ("2-IT") converts free amines on the surface of the protein to sulfhydryl groups. These sulfhydryl groups are then available for reaction with a thiol reactive moiety, such as a maleimide.

"Unliganded hemoglobin" refers to any hemoglobin containing at least one heme moiety that is not liganded to a molecular gas such as oxygen, carbon monoxide or nitric oxide. As such, the hemoglobin is considered "unliganded" if only one of the heme moieties is not liganded to a molecular gas.

The term "heme protein" as used herein to any single or multiple chain protein that bears a heme moiety that binds gases, such as oxygen, nitric oxide or carbon monoxide.

The term "nitroxide" as used herein refers to stable nitroxide free radicals, their precursors and derivatives thereof. This term is not to be confused with nitric oxide donor molecules.

DESCRIPTION OF THE INVENTION

The present invention generally relates to succinimide-activated nitroxyl compounds that can be used to nitroxylate proteins. For example, such nitroxyl compounds can be used to nitroxylate a heme protein such as hemoglobin. Nitroxylation of a heme protein with the succinimide-activated nitroxyl compounds counteracts the oxidation of NO and other biomolecules by oxidative substances, such as superoxide and hydrogen peroxide. The polynitroxylated heme proteins of the present invention are useful as (OTAs) that are capable of delivering molecular oxygen, carbon monoxide, nitric oxide, and mixtures thereof.

Succinimidyl Nitroxide Reagents

The present invention relates to succinimidyl nitroxide reagents that can be used to nitroxylate the amino groups of proteins. The succinimidyl nitroxide reagents generally comprise a succinimide linked to a nitroxide group, for example a TEMPO (2,2,6,6-tetramethyl-piperidine-1-oxyl) or PROXYL (2,2,5,5-tetramethylpyrrolidine-N-oxyl) nitroxide group. The linkage between the succinimide and the nitroxide can be, for example, a carboxy linkage or a carbonate linkage. Such reagents, for example nitroxyl succinimidyl carbonates, are highly reactive, making coupling between the amines of proteins and succinimide highly efficient.

For example, the present invention relates to a nitroxylating agent of formula (I):

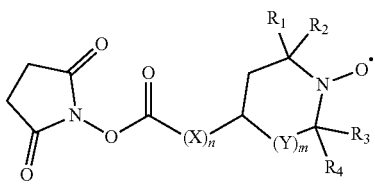
(I)

wherein each of $R_1$, $R_2$, $R_3$, and $R_4$ is independently $C_1$-$C_4$ alkyl; X is oxygen, sulfur, nitrogen, phosphorus, or silicon; Y is $CH_2$; n is 0 or 1; and m is 0 or 1.

The nitroxylating agent of formula (I) can have a structure wherein X, Y, n, and m are as defined above and each of $R_1$, $R_2$, $R_3$, and $R_4$ is —$CH_3$.

Also, the nitroxylating agent of formula (I) can have a structure wherein $R_1$, $R_2$, $R_3$, $R_4$, Y, n, and m are as defined above and X is oxygen or sulfur.

Further, the nitroxylating agent of formula (I) can have a structure wherein $R_1$, $R_2$, $R_3$, $R_4$, Y, n, and m are as defined above and X is oxygen.

The nitroxylating agent of formula (I) can also have a structure wherein Y, n, and m are as defined above, X is oxygen and each of $R_1$, $R_2$, $R_3$, and $R_4$ is —$CH_3$.

Additionally, the nitroxylating agent of formula (I) can have a structure wherein $R_1$, $R_2$, $R_3$, $R_4$, Y, and m are as defined above and n is 0.

The nitroxylating agent of formula (I) can also have a structure wherein $R_1$, $R_2$, $R_3$, $R_4$, Y, and m are as defined above and n is 1.

Further, the nitroxylating agent of formula (I) can have a structure wherein $R_1$, $R_2$, $R_3$, $R_4$, Y, and n are as defined above and m is 0.

The nitroxylating agent of formula (I) can also have a structure wherein $R_1$, $R_2$, $R_3$, $R_4$, Y, and n are as defined above and m is 1.

For example, the nitroxylating agent of formula (I) can be selected from 4-Succinimidyl-TEMPO-Carbonate (4-STC), 3-Succinimidyl-PROXYL-Carbonate (3-SPC), 4-succinimidyl-carboxy-TEMPO (4-SCT), and 3-Succinimidyl-Carboxy-PROXYL (3-SCP). The structures of each of these compounds is shown below:

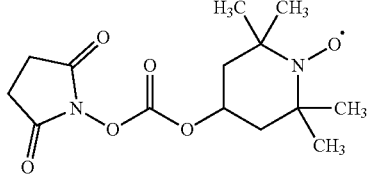

4-Succinimidyl-TEMPO-Carbonate (4-STC; 1-(((2,2,6,6-tetramethyl-1-piperidinyloxy)-4-oxycarbonyl)oxy)-2,5-pyrrolidinedione)

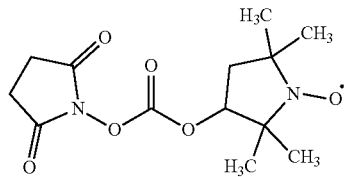

3-Succinimidyl-PROXYL-Carbonate (3-SPC;1-(((2,2,5,5-tetramethyl-1-pyrrolidinyloxy)-3-oxycarbonyl)oxy)-2,5-pyrrolidinedione)

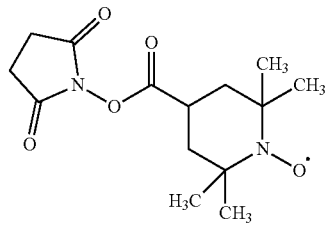

4-succinimidyl-carboxy-TEMPO (4-SCT; 1-(((2,2,6,6-tetramethyl-1-piperidinyloxy)-4-carbonyl)oxy)-2,5-pyrrolidinedione)

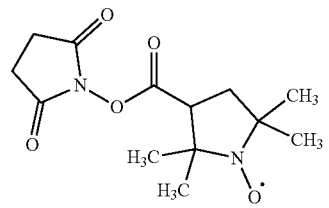

3-Succinimidyl-Carboxy-PROXYL (3-SCP; 1-(((2,2,5,5-tetramethyl-1-pyrrolidinyloxy)-3-carbonyl)oxy-2,5-pyrrolidinedione).

For example, the nitroxylating agent of formula (I) can have the following structure:

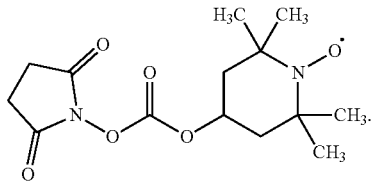

Methods for the Synthesis of Succinimidyl Nitroxide Reagents

The succinimidyl nitroxide reagents can be synthesized using simple one-step activation chemistry using readily available reagents. Furthermore, the activation reaction can be performed under mild conditions.

Thus, the invention further relates to a method for preparing a nitroxylating agent of the formula (II):

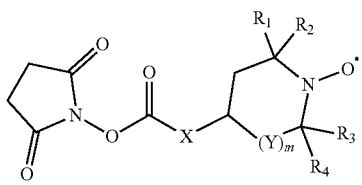
(II)

comprising reacting a compound having the formula (III)

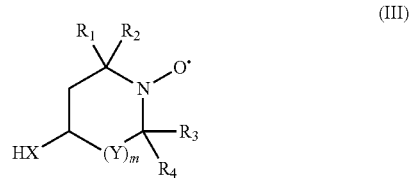

with N,N'-disuccinimidyl carbonate (DSC) in the presence of an organic base; wherein each of $R_1$, $R_2$, $R_3$, and $R_4$ is independently $C_1$-$C_4$ alkyl; X is oxygen, sulfur, nitrogen, phosphorus, or silicon; Y is $CH_2$; and m is 0 or 1.

The method for preparing a nitroxylating agent of the formula (II) can have structures of Formulae (II) and (III) wherein X, Y, and m are as defined above and each of $R_1$, $R_2$, $R_3$, and $R_4$ is —$CH_3$.

The method for preparing a nitroxylating agent of the formula (II) can have structures of Formulae (II) and (III) wherein $R_1$, $R_2$, $R_3$, and $R_4$, Y, and m are as defined above and X is oxygen or sulfur.

The method for preparing a nitroxylating agent of the formula (II) can have structures of Formulae (II) and (III) wherein $R_1$, $R_2$, $R_3$, and $R_4$, Y, and m are as defined above and X is oxygen.

The method for preparing a nitroxylating agent of the formula (II) can have structures of Formulae (II) and (III) wherein Y and m are as defined above, X is oxygen and each of $R_1$, $R_2$, $R_3$, and $R_4$ is —$CH_3$.

The method for preparing a nitroxylating agent of the formula (II) can have structures of Formulae (II) and (III) wherein $R_1$, $R_2$, $R_3$, and $R_4$, X, and Y are as defined above and m is 0.

The method for preparing a nitroxylating agent of the formula (II) can have structures of Formulae (II) and (III) wherein $R_1$, $R_2$, $R_3$, and $R_4$, X, and Y are as defined above and m is 1.

The method for preparing a nitroxylating agent of the formula (II) can have structures of Formulae (II) and (III) wherein $R_1$, $R_2$, $R_3$, and $R_4$, X, Y, and m are as defined above, and wherein the organic base comprises triethylamine (TEA), N,N-diisopropylethylamine, 4-dimethylaminopyridine, pyridine, N-methylpiperidine, or a combination thereof.

The method for preparing a nitroxylating agent of the formula (II) can have structures of Formulae (II) and (III) wherein $R_1$, $R_2$, $R_3$, and $R_4$, X, Y, and m are as defined above and wherein the organic base comprises triethylamine.

The method for preparing a nitroxylating agent of the formula (II) can have structures of Formulae (II) and (III) wherein $R_1$, $R_2$, $R_3$, and $R_4$, X, Y, and m are as defined above, wherein the organic base comprises triethylamine, and wherein the compound of formula (III), the N,N'-disuccinimidyl carbonate, and the triethylamine are present in a ratio of about 1:2:3.

In any of the above methods for preparing a nitroxylating agent of the formula (II), the reaction can be carried out at a temperature of about 2° C. to about 30° C.; about 15° C. to about 25° C.; about 4° C.; or about 20° C.

In any of the above methods for preparing a nitroxylating agent of the formula (II), the reaction can be allowed to proceed for about three to about six hours.

In any of the above methods for preparing a nitroxylating agent of the formula (II), the reaction can be carried out in a polar aprotic solvent. The polar aprotic solvent can comprise acetonitrile (ACN), tetrahydrofuran (THF), ethyl acetate (EtOAc), acetone, dimethylformamide (DMF), dimethyl sulfoxide (DMSO), or a combination thereof. For example, the polar aprotic solvent can comprise acetonitrile.

A reaction scheme for the preparation of 4-Succinimidyl-TEMPO-Carbonate is shown below.

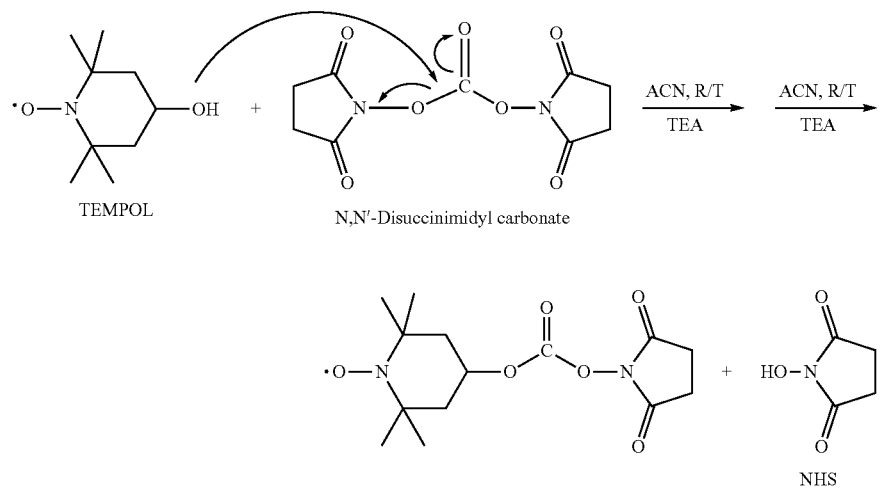

As shown above, 4-hydroxy-TEMPO (4-Hydroxy-2,2,6,6-tetramethylpiperidine 1-oxyl) is used to prepare 4-succinimidyl-TEMPO-carbonate using one-step activation chemistry. Activation of TEMPOL to 4-Succinimidyl-TEMPO-Carbonate is achieved by reaction of TEMPOL with N,N'-Disuccinimidyl-Carbonate in presence of triethylamine. The organic base (TEA in the reaction scheme above) is used as a catalyst that deprotonates the —OH group of the hydroxyl nitroxide (TEMPOL in the reaction scheme above), making it more reactive such that it can act as a nucleophile and attack the electrophilic carbonyl of N,N'-Disuccinimidyl-Carbonate (DSC).

The invention is also directed to a method for preparing a nitroxylating agent of the formula (IV):

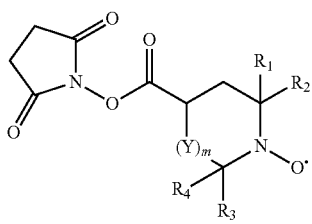

(IV)

comprising reacting a compound having the formula (V)

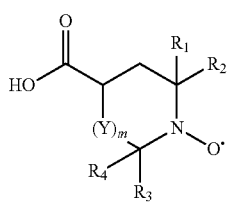

(V)

with N-hydroxysuccinimide (NHS) in the presence of N,N'-dicyclohexylcarbodiimide (DCC); wherein each of $R_1$, $R_2$, $R_3$, and $R_4$ is independently $C_1$-$C_4$ alkyl; Y is $CH_2$; and m is 0 or 1.

The method for preparing a nitroxylating agent of the formula (IV) can use structures of formulae (IV) and (V) wherein Y and m are as defined above in connection with formulae (IV) and (V) and wherein each of $R_1$, $R_2$, $R_3$, and $R_4$ is independently —$CH_3$.

In the method for preparing a nitroxylating agent of the formula (IV), the compound of formula (IV), the N-hydroxysuccinimide, and the N,N'-dicyclohexylcarbodiimide can be present in a reaction mixture in a molar ratio of about 1:1.1:1.1.

The method for preparing a nitroxylating agent of the formula (IV) can use structures of formulae (IV) and (V) wherein Y and $R_1$, $R_2$, $R_3$, and $R_4$ are as defined above in connection with formulae (IV) and (V) and m is 0. The method can also use structures wherein m is 1.

In any of the above methods for preparing a nitroxylating agent of the formula (IV), the reaction is carried out at a temperature of about 2° C. to about 30° C.; about 15° C. to about 25° C.; about 4° C.; or about 20° C.

In any of the above methods for preparing a nitroxylating agent of the formula (IV), the reaction can be allowed to proceed for about 6 to about 24 hours.

In any of the above methods for preparing a nitroxylating agent of the formula (IV), the reaction can carried out at a pH of about 7.2 to about 7.6; or at a pH of about 7.4.

Nitroxylated Proteins and Nitroxylated PAO-Modified Proteins

The present invention also relates to nitroxylated proteins which have at least one nitroxylated amino group. The nitroxylated proteins are also optionally conjugated to one or more a polyalkylene oxide (PAO) molecules, e.g., to one or more polyethylene glycol (PEG) molecules.

Polyethylene oxides for use in conjugating proteins include, but are not limited to, polyethylene oxide, polypropylene oxide and a polyethylene/polypropylene oxide copolymer. The PAO has a molecular weight of about 2,000 to about 20,000 Daltons, preferably from about 3,000 to about 10,000 Daltons, more preferably from 4,000 to about 6,000 Daltons, and most preferably about 5,000 Daltons. The most common PAO presently used to modify the surface of proteins is PEG because of its pharmaceutical acceptability and commercial availability. PEG is available in a variety of molecular weights based on the number of repeating subunits of ethylene oxide (i.e. —$CH_2CH_2O$—) within the molecule, to achieve a desired molecular weight based on the number and size of the PEG molecules conjugated to a protein.

One or both of the terminal end groups of the PAO polymer are converted into a reactive functional group ("activated"). For example, PEG-OH has been used to prepare PEG-halide, mesylate or tosylate, which is then converted to PEG-amine ("PEG-$NH_2$") by performing a nucleophilic displacement reaction with aqueous ammonia (Zalipsky, S. et al., 1983, Eur. Polym. J. 19:1177-1183), sodium azide or potassium phthalimide. The activated PEG can then be conjugated to a protein through the interaction of the PEG amine group (—"$NH_2$") with a carboxyl group ("—COOH") of the protein.

In addition to functionalizing PEG with an amine group and converting it to a maleimide group, PEGs that are activated therewith, are known to be used in the art. For example, PEG may be activated with p-nitrophenyl carbonate, aldehyde, aminopropyl, aminoethyl, thiol, aminoxy, hydrazide, and iodoacetamide, to name a few. Such functional PEG can be conjugated to the surface amino acid side chains of proteins using known methods.

PEG-$NH_2$ can be further functionalized to conjugate with groups other than carboxyl. For example, U.S. Pat. No. 6,828,401 discloses the reaction of PEG-$NH_2$ with maleimide to form mPEG-maleimide. In this reaction, mPEG-OH is reacted with a tosylating reagent (p-toluenesulfonyl chloride) and a base catalyst (triethyleneamine) in the presence of an organic solvent (dichloromethane) to produce mPEG-tosylate. The mPEG-tosylate is then reacted with 28% ammonia water and maleic acid anhydride in an organic solvent mixture of N, N-dimethylacetamide ("DMAc") and N-cyclohexylpyrrolidinone ("CHP") to produce a maleamic acid compound. This compound is then reacted with pentafluorophenyltrifluoroacetate in the presence of dichloromethane to produce the mPEG-maleimide.

Alternatively, mPEG-maleimide can be made by reacting mPEG-OH with a tosylating reagent (p-toluenesulfonyl chloride) and a base catalyst (triethyleneamine) in the presence of an organic solvent (dichloromethane) to produce mPEG-tosylate. The mPEG-tosylate is then reacted with 28% ammonia to prepare mPEG-$NH_2$. The mPEG-$NH_2$ is then reacted with N-methoxy carbonyl maleimide (MCM) in the presence of saturated sodium hydrocarbonate ($NaHCO_3$) to produce mPEG-maleimide.

Non-limiting examples of amino acid residue side chains of human Hb that can be modified using amine reactive chemistry for conjugation to PAO are presented in Table 1 below:

TABLE 1

Amine Reactive Chemistry and Potential Sites of Modification

| Residues | Positions | Reacts With |
|---|---|---|
| α-chain | | |
| Lys | 7, 11, 16, 40, 56, 60, 61, 90, 99, 127 and 139 | Succinimide; NPC (p-nitrophenyl carbonate); isocyanate; aldehyde; isothiocyanate; epoxides. |

TABLE 1-continued

Amine Reactive Chemistry and Potential Sites of Modification

| Residues | Positions | Reacts With |
|---|---|---|
| His | 20, 45, 50, 58, 72, 87, 112 and 122 | Succinimide; NPC (p-nitrophenyl carbonate); isocyanate; aldehyde; isothiocyanate; epoxides. |
| Val | 1 | Succinimide; NPC (p-nitrophenyl carbonate); isocyanate; aldehyde; isothiocyanate; epoxides. |
| β-chain | | |
| Lys | 8, 17, 59, 61, 65, 66, 82, 95, 120, 132 and 144 | Succinimide; NPC (p-nitrophenyl carbonate); isocyanate; aldehyde; isothiocyanate; epoxides. |
| His | 2, 63, 77, 92, 97, 116, 117, 143 and 146 | Succinimide; NPC (p-nitrophenyl carbonate); isocyanate; aldehyde; isothiocyanate; epoxides. |
| Val | 1 | Succinimide; NPC (p-nitrophenyl carbonate); isocyanate; aldehyde; isothiocyanate; epoxides. |

One method to increase the number of available conjugation sites on Hb is to introduce sulfhydryl groups (also known as thiolation), which tend to be more reactive with MalPEG than free amines. A variety of methods are known for protein thiolation. In one method, protein free amines are reacted with succinimidyl 3-(2-pyridyldithio) propionate followed by reduction with dithiothreitol ("DTT"), or tris (2-carboxyethyl)phosphine ("TCEP"). This reaction releases the 2-pyridinethione chromophore, which can be used to determine the degree of thiolation. Amines can also be indirectly thiolated by reaction with succinimidylacetylthioacetate, followed by 50 mM hydroxylamine, or hydrazine at near-neutral pH.

Another method described in U.S. Pat. No. 5,585,484 maintains the positive charge of the amino (α- or ε-) group of the Hb after conjugation. This method involves amidination of the ε-amino groups of Hb by 2-IT to introduce sulfhydryl groups onto the protein. This approach has at least two additional advantages over the previously used succinimidyl chemistry: 1) the high reactivity and selectivity of maleimide groups with sulfhydryl groups facilitates the near quantitative modification of the thiols, with a limited excess of reagents and 2) the thiol group of 2-IT is latent and is generated only in situ as a consequence of the reaction of the reagent with the protein amino groups. These advantages provide one additional benefit; they allow simultaneous incubation of Hb with both the thiolating and PEGylation reagent for surface decoration.

For example, MalPEG can be conjugated to Hb by thiolating an amine of the Hb to introduce thiol groups on the surface of the Hb. The two intrinsic thiol groups of Hb that are available for reaction are at βCys93, and added thiol groups on the surface of the Hb can react with the maleimide of the maleimidyl PAO to form a pegylated Hb conjugate.

The maleimide-PEG includes a linker to attach the maleimide to the PEG. Linkers can include, but are not limited to, alkylene such as ethylene, propylene, or isopropylene, phenylene, amide (—NH—C(O)—), or phenyl carbamate (e.g., —Ph—NH—C(O)—).

Non-limiting examples of amino acid residue side chains that can be modified using thiol reactive chemistry are presented in Table 2 below:

TABLE 2

Thiol Reactive Chemistry and Potential Sites of Modification

| Residues | Positions | Reacts With |
|---|---|---|
| α-chain | | |
| Cys | 104 | Maleimide; iodoacetamide; orthopyridyl-disulfide (OPSS); vinylsulfone. |
| β-chain | | |
| Cys | 93 and 112 | Maleimide; iodoacetamide; orthopyridyl-disulfide (OPSS); vinylsulfone. |

The molecular weight of the PAO-Hb can be regulated by the conjugation reaction. Conventional thought suggested that increasing the molar ratios of the reactants would increase the number of PEG molecules bound to Hb. This included both the thiolation process of Hb (i.e. increasing the molar ratio of thiolating agent to Hb) and the conjugation process (i.e. increasing the molar ratio of thiol activated PEG to thiolated Hb). However, these excess molar ratios resulted in the binding of only 6±1 PEG molecules per Hb (see U.S. Pat. No. 7,501,499).

Recently it was determined that a greater number of PAO molecules could be bound to Hb using lower molar ratios of reactants. The number of available thiol groups on Hb, before and after thiolation and after conjugation, was determined using the dithiopyridine colorimetric assay (Ampulski, R. S. et al., 1969, Biochem. Biophys. Acta 32:163-169). Human Hb contains two intrinsic, reactive thiol groups at the β93cysteine residues, which was confirmed by the dithiopyridine reaction. After thiolation of SFH with 2-IT, the number of reactive thiol groups increased from two to over seven. In this example, an average of 8 PEG molecules was bound to Hb. This was achieved using a 7.5-fold molar excess of 2-IT over SFH in the thiolation reaction and a 12-fold molar excess of MalPEG over thiolated Hb in the conjugation reaction.

Hemoglobin is conjugated with polyalkylene oxide when it is in the oxygenated state to increase the oxygen affinity of the Hb-PAO conjugate.

Nitroxylated Proteins

The nitroxylated proteins have at least one nitroxylated amino group. The nitroxylated protein comprises at least one nitroxylated amino group and the nitroxylated protein can have the structure (VI):

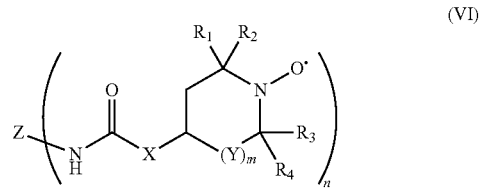

(VI)

wherein Z represents the protein; each of $R_1$, $R_2$, $R_3$, and $R_4$ are independently $C_1$-$C_4$ alkyl; X is oxygen, sulfur, nitrogen, phosphorus, or silicon; Y is $CH_2$; m is 0 or 1; n is the average number of activated-PEG polymers conjugated to the protein, the —NH-group is an amine group of the protein, and N is a nitrogen of the protein.

The nitroxylated protein can comprise at least one nitroxylated amino group, the nitroxylated protein can have the structure (VI) wherein $R_1$, $R_2$, $R_3$, $R_4$, Y, m, n, and Z are as defined above in connection with formula (VI) and X is oxygen or sulfur.

The nitroxylated protein can comprise at least one nitroxylated amino group, the nitroxylated protein can have the structure (VI) wherein $R_1$, $R_2$, $R_3$, $R_4$, Y, m, n, and Z are as defined above in connection with formula (VI) and X is oxygen.

The nitroxylated protein can comprise at least one nitroxylated amino group, the nitroxylated protein can have the structure (VI) wherein Y, m, n, and Z are as defined above in connection with formula (VI), X is oxygen, and each of $R_1$, $R_2$, $R_3$, and $R_4$ is —$CH_3$.

The nitroxylated protein can comprise at least one nitroxylated amino group, the nitroxylated protein having the structure (VII):

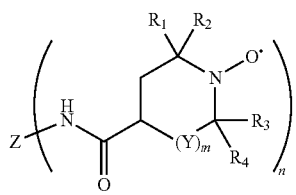

(VII)

wherein Z represents the protein; each of $R_1$, $R_2$, $R_3$, and $R_4$ are independently $C_1$-$C_4$ alkyl; Y is $CH_2$; m is 0 or 1; n is the average number of activated-PEG polymers conjugated to the protein; the —NH-group is an amine group of the protein; and N is a nitrogen of the protein.

The nitroxylated protein can comprise at least one nitroxylated amino group, the nitroxylated protein can have the structure (VI) or (VII) wherein X, Y, m, n, and Z are as defined in connection with formula (VI) or (VII) and each of $R_1$, $R_2$, $R_3$, and $R_4$ is —$CH_3$.

The nitroxylated protein can comprise at least one nitroxylated amino group, the nitroxylated protein having the structure (VI) or (VII) wherein $R_1$, $R_2$, $R_3$, $R_4$, X, Y, M, n, and Z are defined as in connection with formula (VI) or (VII) and m is 0.

The nitroxylated protein can comprise at least one nitroxylated amino group, the nitroxylated protein having the structure (VI) or (VII) wherein $R_1$, $R_2$, $R_3$, $R_4$, X, Y, M, n, and Z are defined as in connection with formulae (VI) or (VII) and wherein m is 1.

In any of the above nitroxylated proteins, the at least one nitroxylated amino group can be the N-terminal amino group of the protein or an epsilon (ε)-amino group of a lysine residue.

The nitroxylated proteins can suitably be polynitroxylated proteins. For example, for nitroxylated proteins having structures of formulae (VI) or (VII), n is about 1 to about 25; n is at least about 2; n is at least about 5; n is at least about 10; or n is about 15 to about 20.

The polynitroxylated protein can be a polynitroxylated heme protein.

Heme proteins are useful in the practice of the present invention. In addition to tetrameric hemoglobin (Hb), this includes single chain (monomeric) natural or recombinant heme proteins, such as those described in BMC Structural Biology, 11:13, which is accessible at http://www.biomed-central.com/content/pdf/1472-6807-11-13.pdf. Other examples of heme proteins can be found in The Journal of Experimental Biology, 201: 1085-1098 (1998).

A variety of Hbs may be utilized with the present invention. The Hb may be obtained from animal sources, such as human, bovine, porcine, or equine hemoglobin. Human Hb is preferred. The Hb can be obtained from natural sources or can be produced by known recombinant methods.

The hemoglobins of the present invention have a high oxygen affinity greater than that of stroma-free hemoglobin. This means that the hemoglobins will have a $P_{50}$ less than 15 mmHg as measured at 37° C. and pH 7.4, preferably from about 2 to about 10 mmHg, and most preferably from about 2 to about 8 mmHg or about 2 to about 5 mmHg.

For example, the nitroxylated protein can comprise a hemoglobin α-subunit, a hemoglobin β-subunit, a hemoglobin tetramer, or a myoglobin.

The nitroxylated protein can comprise a hemoglobin α-subunit, a hemoglobin β-subunit, a hemoglobin tetramer, a myoglobin, or an albumin.

Where the nitroxylated protein is an albumin, the nitroxylated protein can comprise a serum albumin. The serum albumin can comprise human serum albumin (HSA). HSA is a single polypeptide having 585 amino acids. BSA contains 60 lysines, 17 pairs of disulfide bridges and one free cysteine, and has a molecular weight of approximately ~67 kD.

The nitroxylated protein can comprise a hemoglobin α-subunit or a hemoglobin β-subunit or hemoglobin tetramer. The nitroxylated protein can comprise an animal hemoglobin α-subunit, an animal hemoglobin β-subunit, or a hemoglobin tetramer comprising animal hemoglobin α-subunits and β-subunits.

The nitroxylated protein can comprise a human hemoglobin α-subunit, an human hemoglobin β-subunit, or a hemoglobin tetramer comprising human hemoglobin α-subunits and β-subunits.

Where the nitroxylated protein is a hemoglobin tetramer, the hemoglobin can be intramolecularly cross-linked. Intramolecularly crosslinked hemoglobins prevent dissociation into dimers and to avoid being cleared by the kidneys, extending circulation half-life. A variety of methods are known in the art for intramolecularly crosslinking Hb. Chemical crosslinking reagents include glutaraldehyde (U.S. Pat. No. 7,005,414), polyaldehydes (U.S. Pat. No. 4,857,636), diaspirin (U.S. Pat. No. 4,529,719), pyridoxyl-5'-phosphate (U.S. Pat. No. 4,529,719) trimesoyltris(methyl phosphate) (U.S. Pat. No. 5,250,665), dialkynes (for reaction with hemoglobin having an azide linker. See Foot et al., Chem. Commun. 2009, 7315-7317; Yang et al., Chem. Commun. 2010, 46: 7557-7559) and hemoglobins can be crosslinked via recombinant methodologies.

For example, the hemoglobin tetramer can comprise a cross-linked αα dimer or a cross-linked ββ dimer.

As shown in Table 1 above, the α- and β-subunits of human hemoglobin N-terminal valine residues that can be nitroxylated on the N-terminal amino group. In addition, the α- and β-subunits of human hemoglobin contain a number of lysine groups that can be nitroxylated at the ε-amino group.

Additionally, the nitroxylated protein can comprise a human hemoglobin α-subunit. The human hemoglobin α-subunit can be nitroxylated at the α-amino group of the N-terminal valine residue. Further, the human hemoglobin α-subunit can be nitroxylated at the ε-amino group of a lysine residue selected from the group consisting of lysine-7, lysine-11, lysine-16, lysine-40, lysine-56, lysine-60, lysine-61, lysine-90, lysine-99, lysine-127, lysine-139, and a combination thereof.

The nitroxylated protein can also comprise a human hemoglobin β-subunit. The human hemoglobin β-subunit can be nitroxylated at the α-amino group of the N-terminal valine residue. The human hemoglobin β-subunit can also be nitroxylated at the ε-amino group of a lysine residue selected from the group consisting of lysine-8, lysine-17, lysine-59, lysine-61, lysine-65, lysine-66, lysine-82, lysine-95, lysine-120, lysine-132, lysine-144, and a combination thereof.

Further, nitroxylated protein can comprise a hemoglobin tetramer and the hemoglobin tetramer can comprise about seventeen nitroxylated amino groups.

Nitroxylated and PAO-Conjugated Proteins

The nitroxylated protein can also be conjugated to a polyalkylene oxide (PAO). The PAO can be a polyethylene glycol (PEG).

The PEG can have an average molecular weight of about 2,000 to about 20,000 Daltons; about 3,000 to about 10,000 Daltons; about 4,000 to about 6,000 Daltons; or about 5,000 Daltons.

The nitroxylated protein can also be conjugated to a PEG that is a maleimide-PEG. The maleimide can be linked to the PEG via an alkylene or phenylene linker. The alkylene linker can be an ethylene linker.

Also, the nitroxylated protein can have a conjugated PEG that is a maleimide-PEG conjugated to a thiol moiety of the protein selected from the group consisting of an intrinsic thiol moiety of a cysteine residue of the protein, a thiol moiety of a thiolated lysine residue of the protein, and a combination thereof.

The nitroxylated protein can have a conjugated PEG that is a maleimide-PEG, wherein the maleimide-PEG conjugated to an intrinsic thiol moiety of a cysteine residue or conjugated to a thiol moiety of a thiolated lysine residue has the structure (VIII)

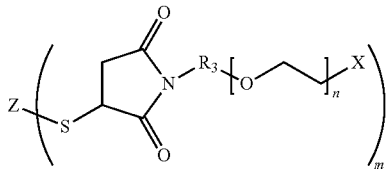

(VIII)

wherein Z represents the protein, S is the thiol group of the protein, $R_3$ is an alkylene or phenylene group, X is a terminal group, m is the average number of activated-PEG polymers conjugated to the protein, and n represents the average number of oxyethylene units of a PEG having an average molecular weight of about 2,000 to about 20,000 Daltons.

The nitroxylated protein can have the structure of formula (VIII) wherein $R_3$ is ethylene.

The nitroxylated protein can have the structure of formula (VIII) wherein m is about 6 to about 10.

The nitroxylated protein can have the structure of formula (VIII) wherein X is methoxy (—OCH$_3$) or carboxylate (—COOH).

The nitroxylated protein can have the structure of formula (VIII) wherein the maleimide-PEG is conjugated to a thiol moiety of a cysteine-93 residue of a hemoglobin β-subunit.

The nitroxylated protein having the structure of formula (VIII) wherein the maleimide-PEG is conjugated to a thiol moiety of a thiolated lysine residue of a hemoglobin α-subunit or β-subunit. The nitroxylated protein having the structure of formula (VIII) wherein the thiolated lysine residue is a thiolated lysine residue of a human hemoglobin α-subunit selected from the group consisting of lysine-7, lysine-11, lysine-16, lysine-40, lysine-56, lysine-60, lysine-61, lysine-90, lysine-99, lysine-127, lysine-139, and a combination thereof. The nitroxylated protein of formula (VIII) wherein the thiolated lysine residue is a thiolated lysine residue of a human hemoglobin β-subunit selected from the group consisting of lysine-8, lysine-17, lysine-59, lysine-61, lysine-65, lysine-66, lysine-82, lysine-95, lysine-120, lysine-132, lysine-144, and a combination thereof.

Nitroxylated Hemoglobin Tetramers

A hemoglobin tetramer comprising at least one α-subunit or at least one β-subunit of any one of the nitroxylated hemoglobins described herein.

These hemoglobin tetramers can have at least one α-subunit and at least one β-subunit of any one of the nitroxylated hemoglobins described herein.

The hemoglobin tetramers can comprise two α-subunits and two β-subunits of any one of the nitroxylated hemoglobins described herein.

The hemoglobin tetramers described herein wherein the hemoglobin is conjugated to on average 5 to 10 PAO molecules per tetramer, the hemoglobin is conjugated to on average 7.1 to 8.9 PAO molecules per tetramer.

The hemoglobin tetramer wherein the hemoglobin is oxygenated.

The hemoglobin tetramer wherein the hemoglobin is deoxygenated.

The hemoglobin tetramer wherein the hemoglobin is liganded with CO, NO, or a mixture of CO and NO.

The hemoglobin conjugates of the invention can be in oxygenated or deoxygenated form, can be liganded to CO or NO, or can be a mixture including two or more of these four forms. HbO$_2$ is prepared by equilibrating non-oxygenated hemoglobin with air, pure O$_2$ gas or O$_2$/nitrogen gas mixtures.

Deoxygenation can be performed by any method known in the art. One simple method is to expose the hemoglobin solution to an inert gas, such as nitrogen, argon or helium. To assure that deoxygenation is relatively homogeneous, the Hb solution is circulated in this process. Monitoring deoxygenation to attain desired levels may be performed by using a Co-oximeter 682 (Instrument Laboratories). If partial reoxygenation is desired, deoxygenated Hb may be exposed to oxygen or to a gas mixture containing oxygen, such as air.

Gas exchange to replace molecular oxygen with another gas may be accomplished through a gas-permeable membrane, such as a polypropylene or cellulose acetate membrane. See, for example, published U.S. Patent Application No. 2006/0234915. Commercially available gas-exchange devices utilizing these membranes include the Celgard™ polypropylene microporous hollow fiber device from Hoechst-Celanese (Dallas, Tex.) or the Cell-Pharm™ hollow fiber oxygenator from American Laboratory (East Lyme, Conn.). In the Hoechst-Celanese Celgard™ device, oxygenated Hb is deoxygenated by passing an aqueous Hb solution through polypropylene microporous hollow filters at 10-100 ml/min/ft² while the system is purged with nitrogen at 5-20 psi. The Hb is generally circulated for about 5 to 30 minutes to achieve the desired percentage of deoxyHb. Another method for producing deoxygenated Hb comprises exposing a Hb solution to a chemical reducing agent such as sodium ascorbate, sodium dithionate and sodium bisulfite. Hb is partially deoxygenated by adjusting the reducing agent concentration, reaction time and temperature. Alternatively, a reducing agent may be used to substantially deoxygenate Hb, and then oxygen may be reintroduced to form a partially deoxygenated product. For example, Hb can be exposed to a 100 mM concentration of sodium bisulfite for about one hour before adding antioxidants.

Hb can be liganded to CO using any known methods for forming oxyhemoglobin, simply by substituting CO for $O_2$. This generally involves introducing a source of CO to a solution of hemoglobin such that the hemoglobin becomes liganded with CO instead of $O_2$ (K. D. Vandegriff, et al., Biochem. J. 382:183-189 (2004)). Since hemoglobin has a higher affinity for CO than it does for oxygen, it is not necessary to first deoxygenate the hemoglobin. Accordingly, the most convenient way of forming CO-Hb complexes is by introducing 100% gaseous CO to a solution of hemoglobin.

HbNO can be prepared by reacting deoxygenated hemoglobin with nitric oxide gas, or by exposing CO-Hb to NO gas such that the NO exchanges for CO. HbNO can also be made by reacting deoxygenated hemoglobin with a small NO-donor molecule like PROLI NONOate™ (i.e., 1-(hydroxy-NNO-azoxy)-L-proline, disodium salt; Cayman Chemical, Ann Arbor, Mich.).

It should be noted that hemoglobin to which NO, a free radical, is bound to the amino acid side groups in the globin chain are not NO-Hb complexes as defined herein, since such compounds do not contain diatomic (nonionic) NO as a ligand in the heme pocket instead of oxygen. For example, nitrosylhemoglobin is formed when native hemoglobin is exposed to a NO donor under conditions that cause it to bind to free sulfhydryl groups (U.S. Pat. No. 6,627,738). Such nitrosylhemoglobins still carry oxygen, whereas the NO-Hb complexes of the present invention do not. Furthermore, when the modified hemoglobin is formed by a reaction directed towards sulfhydryl moieties such as described above, these moieties are no longer available for NO binding.

Methods for the Nitroxylation of Proteins and PAO-Modified Proteins

The present invention also relates to methods for nitroxylation of proteins, including PAO-modified proteins. The methods of the present invention provide site-specific nitroxylation and can be performed under favorable reaction conditions. Nitroxylated-PEGylated hemoglobin produced using these methods has enhanced circulation time and protein stability, as well as a high oxygen affinity.

The nitroxylated protein can be prepared by reacting the protein with a nitroxylating agent of formula (II)

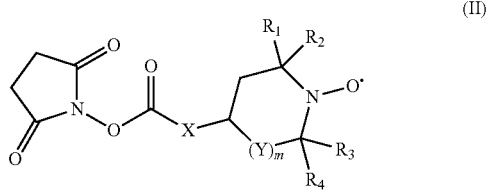

(II)

wherein each of $R_1$, $R_2$, $R_3$, and $R_4$ is independently $C_1$-$C_4$ alkyl; X is oxygen, sulfur, nitrogen, phosphorus, or silicon; Y is $CH_2$; and m is 0 or 1.

The method of making a nitroxylated protein wherein the nitroxylating agent of formula (II) has $R_1$, $R_2$, $R_3$, $R_4$, Y, and m as defined in connection with formula (II) and X is oxygen or sulfur.

The method of making a nitroxylated protein wherein the nitroxylating agent of formula (II) has $R_1$, $R_2$, $R_3$, $R_4$, Y, and m as defined in connection with formula (II) and X is oxygen.

The method of making a nitroxylated protein wherein the nitroxylating agent of formula (II) has Y and m as defined in connection with formula (II) X is oxygen and each of $R_1$, $R_2$, $R_3$, and $R_4$ is —$CH_3$.

A method for preparing a nitroxylated protein comprising reacting the protein with a nitroxylating agent of formula (IV):

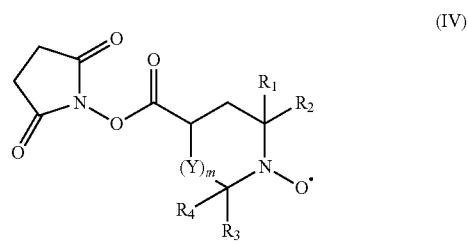

(IV)

wherein each of $R_1$, $R_2$, $R_3$, and $R_4$ is independently $C_1$-$C_4$ alkyl; Y is $CH_2$; and m is 0 or 1. method of claim G2, wherein each of $R_1$, $R_2$, $R_3$, and $R_4$ is independently —$CH_3$.

The method of making a nitroxylated protein wherein the nitroxylating agent of formula (II) or (IV) has X, Y, and m as defined in connection with formula (II) or (IV) and each of $R_1$, $R_2$, $R_3$, and $R_4$ is —$CH_3$.

The method of making a nitroxylated protein wherein the nitroxylating agent of formula (II) or (IV) has $R_1$, $R_2$, $R_3$, $R_4$, X, and Y as defined in connection with formula (II) or (IV) and m is 0.

The method of making a nitroxylated protein wherein the nitroxylating agent of formula (II) or (IV) has $R_1$, $R_2$, $R_3$, $R_4$, X, and Y as defined in connection with formula (II) or (IV) and m is 1.

The method for making a nitroxylated protein wherein the ratio of the nitroxylating agent of formula (II) or (IV) is present at about a 5- to about 100-fold molar excess over the protein.

The method for making a nitroxylated protein using the nitroxylating agent of formula (II) or (IV) wherein the protein comprises an α- or β-subunit of a hemoglobin tetramer. The method where the protein comprises a hemoglobin tetramer. The method wherein the hemoglobin tetramer is a non-oxygenated hemoglobin tetramer. The method wherein the non-oxygenated hemoglobin tetramer is a CO-liganded hemoglobin tetramer. The method wherein the hemoglobin tetramer is a deoxygenated hemoglobin tetramer.

The method for making a nitroxylated protein using the nitroxylating agent of formula (II) or (IV) wherein the reaction is carried out at a temperature of about 2° C. to about 30° C.; about 15° C. to about 25° C.; about 2° C. to about 8° C.; about 4° C.; or about 20° C.

The method for making a nitroxylated protein using the nitroxylating agent of formula (II) or (IV) wherein the reaction is allowed to proceed for about three to about 20 hours; about three to about six hours; or about 16 hours.

The method for making a nitroxylated protein using the nitroxylating agent of formula (II) or (IV) wherein the reaction is carried out in an aqueous solvent.

The method for making a nitroxylated protein using the nitroxylating agent of formula (II) or (IV) wherein the reaction is carried out at a pH of about 6.5 to about 8.5; a pH of about 7.5; or a pH of about 7.2.

The method for making a nitroxylated protein using the nitroxylating agent of formula (II) or (IV) wherein the protein comprises a hemoglobin tetramer, the reaction is carried out at a pH of about 7.2 and a temperature of about 2° C. to about 8° C. and is allowed to proceed for about sixteen hours, and wherein the method yields a nitroxylated hemoglobin tetramer having about 17 nitroxylated amino groups.

The method for making a nitroxylated protein using the nitroxylating agent of formula (II) or (IV) wherein the protein comprises a hemoglobin tetramer, and the nitroxylating agent is present at about a 10- to about 100-fold molar excess over the hemoglobin tetramer.

The method for making a nitroxylated protein of using the nitroxylating agent formula (II) or (IV) wherein the product of the reaction is a nitroxylated protein of formula (VI) or (VII) or a hemoglobin tetramers described herein.

The method for making a nitroxylated protein using the nitroxylating agent of formula (II) or (IV) further comprising conjugating the protein to a polyalkylene oxide (PAO).

The method for making a nitroxylated protein using the nitroxylating agent of formula (II) or (IV) further comprising adding succinimidyl valerate PAO to the protein in the aqueous diluent to form a PAO-valerate conjugated protein. The method further comprising mixing the protein with 2-iminothiolane (2-IT) in an aqueous diluent to form a thiolated protein; and adding PAO-maleimide to the thiolated protein in the aqueous diluent to form a PAO-maleimide conjugated protein. The method wherein the PAO is a polyethylene glycol (PEG).

The method for making a nitroxylated protein using the nitroxylating agent of formula (II) or (IV) further comprising conjugating the protein to a polyalkylene oxide (PAO) and wherein the PAO is a polyethylene glycol (PEG) wherein the PEG has an average molecular weight of about 2,000 to about 20,000 Daltons; about 3,000 to about 10,000 Daltons; about 2,000 to about 6,000 Daltons; or about 5,000 Daltons.

The method for making a nitroxylated protein using the nitroxylating agent of formula (II) or (IV) wherein the PEG is a maleimide-PEG. The method wherein the maleimide is linked to the PEG via an alkylene or phenylene linker. The method wherein the alkylene linker is an ethylene linker. The method wherein the maleimide-PEG is conjugated to a thiol moiety of the protein selected from the group consisting of an intrinsic thiol moiety of a cysteine residue of the protein, a thiol moiety of a thiolated lysine residue of the protein, and a combination thereof.

The method for making a nitroxylated protein using the nitroxylating agent of formula (II) or (IV) wherein the maleimide-PEG conjugated to an intrinsic thiol moiety of a cysteine residue has the structure (VIII)

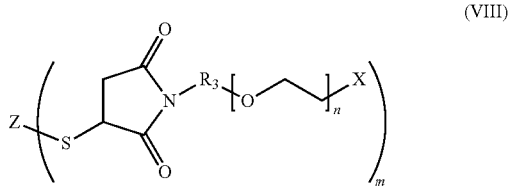

(VIII)

wherein Z represents the protein, $R_3$ is an alkylene or phenylene group, S is the thiol group of the protein, m is the average number of activated-PEG polymers conjugated to the protein, and n represents the average number of oxyethylene units of a PEG having an average molecular weight of about 2,000 to about 20,000 Daltons.

The method wherein the maleimide-PEG conjugated to an intrinsic thiol moiety of a cysteine residue has the structure (VIII) wherein $R_3$ is ethylene. The method wherein the protein comprises a hemoglobin α-subunit, a hemoglobin β-subunit, a hemoglobin tetramer, a myoglobin, or an albumin. The method wherein the protein comprises a serum albumin. The method wherein the serum albumin comprises human serum albumin (HSA). The method wherein the protein comprises a hemoglobin tetramer.

The method wherein the hemoglobin tetramer comprises a cross-linked αα dimer or a cross-linked ββ dimer. The method wherein the maleimide-PEG is conjugated to a thiol moiety of a cysteine-93 residue of a hemoglobin β-subunit. The method wherein the maleimide-PEG is conjugated to a thiol moiety of a thiolated lysine residue of a hemoglobin α-subunit or β-subunit. The method wherein the thiolated lysine residue is a thiolated lysine residue of a human hemoglobin α-subunit selected from the group consisting of lysine-7, lysine-11, lysine-16, lysine-40, lysine-56, lysine-60, lysine-61, lysine-90, lysine-99, lysine-127, lysine-139, and a combination thereof. The method wherein the thiolated lysine residue is a thiolated lysine residue of a human hemoglobin β-subunit selected from the group consisting of lysine-8, lysine-17, lysine-59, lysine-61, lysine-65, lysine-66, lysine-82, lysine-95, lysine-120, lysine-132, lysine-144, and a combination thereof.

The method for making a nitroxylated protein using the nitroxylating agent of formula (II) or (IV) wherein the 2-iminithiolane is present at a concentration of between about 7- and about 15-fold molar excess over the protein concentration; between about 7- and about 8-fold molar excess over the protein concentration; or at about 7-0.5-fold molar excess over the protein concentration.

The method for making a nitroxylated protein using the nitroxylating agent of formula (II) or (IV) wherein the PAO-maleimide is present at a concentration of between about 9- and about 20-fold molar excess over the protein concentration; between about 9- and about 15-fold molar excess over the protein concentration; or about a 12-fold molar excess over the protein concentration.

The method for making a nitroxylated protein using the nitroxylating agent of formula (II) or (IV) wherein the thiolation step is carried out at a pH of between about 7 and about 9; or a pH of about 8.5.

The method for making a nitroxylated protein using the nitroxylating agent of formula (II) or (IV) wherein the step of adding the PAO-maleimide to the thiolated protein to form a PAO-maleimide conjugated protein is carried out at a pH of between about 6.5 and about 8.5; or at a pH of about 7.5.

The method for making a nitroxylated protein using the nitroxylating agent of formula (II) or (IV) wherein the PEG is an SVA-PEG. The method wherein the succinimide is linked to the PEG via —C(O)—(CH$_2$)$_4$—. The SVA-PEG can be conjugated to an amino moiety of the protein selected from an ε-amino moiety of a lysine residue of the protein, an α-amino moiety of a terminal valine residue of the protein, or a combination thereof. The SVA-PEG can also be conjugated to an ε-amino moiety of a lysine residue of the protein or an α-amino moiety of a terminal valine residue of the protein has the structure (IX)

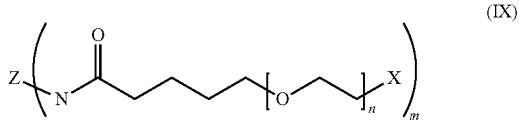

(IX)

wherein Z is the protein, N is a nitrogen of the protein, X is a terminal group, m is the number of activated-PEG polymers conjugated to the protein, and n is the average number of oxyethylene units of a PEG having an average molecular weight of from about 2,000 to about 20,000 Daltons.

X is a terminal group of the PAO, and can be hydroxy, aryloxy such as benzyloxy, or $C_1$-$C_{20}$ alkoxy, more preferably $C_1$-$C_{10}$ alkoxy group, and still more preferably a $C_1$-$C_5$ alkoxy group such as methoxy or ethoxy.

The method for making a nitroxylated protein using the nitroxylating agent of formula (II) or (IV) wherein for formula IX m is on average from about 6 to about 10 PAO molecules per tetramer. The SVA-PEG is conjugated to an ε-amino moiety of a lysine residue of a hemoglobin α-subunit or β-subunit. The SVA-PEG is conjugated to an α-amino moiety of a terminal valine residue of a hemoglobin α-subunit or β-subunit.

The method for making a nitroxylated protein using the nitroxylating agent of formula (II) or (IV) wherein for formula IX the lysine residue is a lysine residue of a human hemoglobin α-subunit selected from the group consisting of lysine-7, lysine-11, lysine-16, lysine-40, lysine-56, lysine-60, lysine-61, lysine-90, lysine-99, lysine-127, lysine-139, and a combination thereof. The lysine residue is a lysine residue of a human hemoglobin β-subunit selected from the group consisting of lysine-8, lysine-17, lysine-59, lysine-61, lysine-65, lysine-66, lysine-82, lysine-95, lysine-120, lysine-132, lysine-144, and a combination thereof.

The method for making a nitroxylated protein using the nitroxylating agent of formula (II) or (IV) wherein the protein is conjugated to PAO prior to nitroxylation of the protein. The step of adding the PAO-maleimide to the thiolated protein to form a PAO-maleimide conjugated protein can be performed concurrently with nitroxylation of the protein. The step of adding the succinimidyl valerate PAO to the protein to form a PAO-valerate conjugated protein is performed concurrently with nitroxylation of the protein.

In any of the above methods, the degree of nitroxyl substitution can be evaluated and quantified using electron paramagnetic resonance (EPR) or MALDI-TOF mass spectroscopy.

Pharmaceutical Compositions

The PAO-Hb conjugates of the present invention can be formulated as a pharmaceutical composition comprising the PAO-Hb conjugate in a pharmaceutically acceptable carrier for parenteral administration, such as an aqueous diluent. The concentration of the PAO-Hb conjugate in the carrier can vary according to the application. Preferably, the PAO-Hb conjugate concentration ranges from about 0.1 g/dl to about 10 g/dl, more preferably from about 2.0 g/dl to about 8.0 g/dl, and most preferably about 4.0 to about 6.0 g/dl. The selection of an appropriate concentration of hemoglobin depends on the colloidal osmotic (oncotic) properties of the final hemoglobin product. Preferably, the compositions of the invention are normo-oncotic as compared to whole blood or hyperoncotic as compared to plasma. The hemoglobin concentration can be adjusted to obtain the desired oncotic pressure for each indication.

When the composition is formulated as a parenteral, the solution generally comprises a physiologically compatible electrolyte carrier isosmotic with whole blood and which maintains the reversible oxygen-, CO- or NO-carrying and delivery properties of the hemoglobin.

The pharmaceutically acceptable carrier can be an aqueous diluent. The aqueous diluent can comprise an aqueous solution of a colloid or an aqueous solution of a non-oxygen carrying component, such as an aqueous solution of proteins such as albumin, an aqueous solution of glycoproteins, an aqueous solution of polysaccharides, or a combination thereof. The aqueous diluent can comprise an aqueous cell-free solution.

Suitable aqueous diluents include, but are not limited to, physiological saline, a saline-glucose mixture, Ringer's solution, lactated Ringer's solution, Locke-Ringer's solution, Krebs-Ringer's solution, Hartmann's balanced saline, heparinized sodium citrate-citric acid-dextrose solution, an acetate solution, a multiple electrolyte solution (e.g., Plasma Lyte® or Plasma Lyte-A® from Baxter International, Deerfield, Ill.), a lactobionate solution, and polymeric plasma substitutes, such as polyethylene oxide, polyvinyl pyrrolidone, polyvinyl alcohol, an ethylene oxide-propylene glycol condensate, or a combination thereof.

The composition can additionally comprise pharmaceutically-acceptable fillers, salts, and other materials well-known in the art, the selection of which depends on the dosage form, the condition being treated, the particular purpose to be achieved according to the determination of the ordinarily skilled artisan in the field and the properties of such additives. For example, the composition can include physiological buffers, carbohydrates (e.g. glucose, mannitol, or sorbitol), alcohols or poly alcohols, pharmaceutically acceptable salts (e.g., sodium or potassium chloride), surfactants (e.g., polysorbate 80), anti-oxidants, anti-bacterial agents, oncotic pressure agents (e.g. albumin or polyethylene glycols) or reducing agents (e.g., ascorbic acid, glutathione, or N-acetyl cysteine).

The pharmaceutical compositions have a viscosity of at least about 2 centipoise (cP). More specifically, the viscosity ranges from about 2 to about 5 cP, and particularly about 2.5 to about 4.5 cP.

In order to avoid complications in administration, the pharmaceutical composition is of high purity, i.e. free from stroma, phospholipids, and pyrogens, having an endotoxin level of no more than 0.25 EU/ml, as measured by the LAL (limulus amebocyte lysate) test, and having less than 8% methemoglobin.

Pharmaceutical compositions can be administered parenterally, such as by subcutaneous, intravenous, or intramuscular injection, or as large volume parenteral solutions. The compositions can also be administered by gavage.

A typical dose of hemoglobin conjugate as a therapeutic agent can be from about 1 to about 15,000 milligrams of hemoglobin per kilogram of patient body weight. For example, when used as an oxygen therapeutic, the dosage will range between 100 to 7500 mg/kg patient body weight, more preferably 500 to 5000 mg/kg body weight, and most preferably 700 to 3000 mg/kg body weight. Thus, a typical dose for a human patient might be from a gram to over 1000 grams. It will be appreciated that the unit content of active ingredients contained in an individual dose of each dosage form need not in itself constitute an effective amount, as the necessary effective amount could be reached by administration of a number of individual doses. The selection of dosage depends upon the dosage form utilized, the condition being treated, and the particular purpose to be achieved according to the determination of those skilled in the art.

Methods of Treatment

The PAO-Hb conjugates and pharmaceutical compositions can be used to deliver oxygen, CO and/or NO to a subject. A method of delivering oxygen, nitric oxide, carbon monoxide or mixtures thereof to tissue and reducing nitrite to produce further endogenous nitric oxide (NO) in the microvasculature includes administering the hemoglobin conjugate or the composition to a subject in need thereof, wherein following administration, the hemoglobin becomes unliganded and converts nitrite to nitric oxide in the microvasculature.

The hemoglobin conjugates and compositions thereof of the invention can be used: to treat acute liver failure, beta thalassemia, a burn, chronic critical limb ischemia, carbon dioxide or cyanide poisoning, chronic obstructive pulmonary disease (COPD) (e.g., acute exacerbations), congestive heart failure (e.g., acute heart failure, chronic heart failure), hypoxia (e.g., high altitude use including for pulmonary edema, decompression sickness), malaria (e.g., cerebral malaria (Falciparum occlusive events), organ ischemia (e.g., acute bowel ischemia (torsion), acute bowel ischemia (embolism), cardiogenic shock, acute vascular organ ischemia, stroke (before CAT scan), stroke (after CAT scan), myocardial infarction/severe cardiac ischemia), peripheral vascular disease, porphyria, pre-eclampsia in pregnancy, sepsis, sickle cell disease (e.g., stroke/transient ischemic attack, splenic sequestration, hepatic sequestration, priapism), retinal disease/intra-ocular condition (e.g., central retinal artery occlusion, central venous occlusion), testicular torsion, trauma/shock (e.g., traumatic hemorrhagic shock, non-traumatic hemorrhagic shock, pre-hospital/field use (military/emergency), traumatic brain injury/blast), ulcers, or vasospasm; as an adjunct to angioplasty, as an adjunct for plastic surgery (skin flaps) (e.g., acute treatment, chronic treatment), or as an adjunct in implanting a ventricular assist device; as a blood substitute (e.g., for acute blood loss, Jehovah's Witness, difficult to cross-match patient, rare blood group, sickle aplastic crisis, sickle cell anemia perioperative management, acute hemolytic anemia (autoimmune), acute hemolytic anemia (toxin), or other refractory anemia), a cardioprotectant, a cryopreservative, a hemodialysis adjunct, an oncology agent (e.g., adjunct to radiotherapy or chemotherapy, solid tumors), an organ preservative (e.g., ex vivo, in donor, in recipient), a performance enhancement agent (e.g., civilian/athletic, military), a surgery adjunct (e.g., cardiopulmonary bypass (prime), cardiopulmonary bypass (adjustment), lung ischemia, pre-surgery conditioning, ruptured aortic aneurysm, replacement of thoracic aorta (dissection or aneurysm)), or a wound healing agent; in imaging (x-ray or magnetic resonance imaging (MM)); to improve lung function (e.g., acute lung injury, chronic lung injury, transient viral pneumonia, neonatal distress syndrome); or a combination thereof. Such uses include administration of the conjugate or composition to a subject in need thereof.

Further, the hemoglobins and compositions of the invention can be used to treat non-traumatic hemorrhagic shock, pre-hospital setting trauma, traumatic hemorrhagic shock, acute lung injury, adult respiratory distress syndrome, traumatic brain injury, stroke, solid tumor cancer, organ degradation (ex-vivo), organ degradation (in recipient), severe sepsis/septic shock, myocardial infarction/cardiac ischemia, cardiogenic shock, acute heart failure, pulmonary embolism, various conditions by surgery (e.g., adjunct to angioplasty, adjunct to thoracic aortic repairs, adjunct to cardiopulmonary bypass, priming solution for cardiopulmonary bypass), or a combination thereof.

The numerous clinical settings in which the hemoglobins and compositions of the present invention are useful include the following:

Trauma. An acute loss of whole blood can result in a fluid shift from the interstitial and intracellular spaces to replace the lost volume of blood while shunting of blood away from the low priority organs including the skin and gut. Shunting of blood away from organs reduces and sometimes eliminates $O_2$ levels in these organs and results in progressive tissue death. The primary goal is to oxygenate affected tissues. This trauma can be in a pre-hospital setting or can result in traumatic hemorrhagic shock or traumatic brain injury.

Ischemia. The conjugates and compositions thereof can also be used to deliver oxygen, CO, and/or NO to areas that red blood cells or many other oxygen therapeutics cannot penetrate. These areas can include any tissue areas that are located downstream of obstructions to red blood cell flow, such as areas downstream of thrombi, sickle cell occlusions, arterial occlusions, angioplasty balloons, surgical instrumentation, and any tissues that are suffering from oxygen starvation or are hypoxic. All types of tissue ischemia can be treated including, for example, stroke, emerging stroke, transient ischemic attacks, myocardial stunning and hibernation, acute or unstable angina, emerging angina, infarct, and the like. In particular, conditions resulting in ischemia include acute heart failure, cardiogenic shock, myocardial infarction/cardiac ischemia, stroke, pulmonary embolism, non-traumatic hemorrhagic shock, or cerebrovascular trauma.

Hemodilution. In this application, the therapeutic is administered to replace (or substitute for) the $O_2$ levels of the removed autologous blood. This permits the use of the removed autologous blood for necessary transfusions during and after surgery. One such surgery requiring pre-operative blood removal would be a cardiopulmonary bypass procedure.

Sepsis/Septic Shock. In sepsis, some patients may become hypertensive in spite of massive fluid therapy and treatment with vasoconstrictor agents. In this instance, the overproduction of nitric oxide (NO) results in lowered blood pressure. Therefore hemoglobin is a desirable agent for treatment of these patients because hemoglobin binds NO with a high avidity.

Hypoxemia. When a patient has acute lung injury caused by either pneumonia or pancreatitis, hypoxemia can be observed and can be alleviated by providing the hemoglobins or compositions of the invention to oxygenate the affected tissues.

Cancer. Delivery of $O_2$ to the hypoxic inner core of a solid tumor mass increases its sensitivity to radiotherapy and chemotherapy. Because the microvasculature of a tumor is unlike that of other tissues, sensitization through increasing $O_2$ levels requires $O_2$ be unloaded within the hypoxic core. In other words, the P50 should be very low to prevent early unloading of the $O_2$, increasing the $O_2$ levels, to insure optimal sensitization of the tumor to subsequent radiation and chemotherapy treatments.

Surgery. The hemoglobins and compositions of the invention can be used during various surgical procedures. For example, they can be used as an adjunct to angioplasty, thoracic aortic repairs, during a cardiopulmonary bypass procedure or as a cardiopulmonary priming solution.

Organ Perfusion. During the time an organ is maintained ex vivo or in an organ donation recipient, maintaining $O_2$ content helps preserve structural and cellular integrity and minimizes infarct formation. The hemoglobins and compositions can sustain the oxygen requirements for such an organ.

The hemoglobins and compositions thereof can also be used in non-humans, such as domestic animals (e.g., livestock and companion animals such as dogs, cats, horses, birds, reptiles. It is contemplated that the present invention finds utility in the emergency treatment of domestic and wild animals suffering a loss of blood due to injury, hemolytic anemias, etc. Veterinary uses include treatment of loss of blood due to injury, hemolytic anemia, equine infectious anemia, feline infectious anemia, bacterial infection, Factor IV fragmentation, hypersplenation and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic anemia, parasitism, or surgical-anesthesia induced brain damage.

EXAMPLES

Example 1. Synthesis of 4-Succinimidyl-TEMPO-Carbonate (4-STC; 1(((2,2,6,6-tetramethyl-1-piperidinyloxy)-4-oxycarbonyl)oxy)-2,5-pyrrolidinedione)

One gram of 4-hydroxy-2,2,6,6-tetramethylpiperidin-1-oxyl (TEMPOL) was dissolved in 20 mL anhydrous acetonitrile and mixed for five minutes at room temperature. Once the TEMPOL dissolved, 2.975 g of N,N'-Disuccinimidyl carbonate (DSC) (2 eq) and 2.425 mL of triethylamine (3.0 eq) were added to the reaction. The reaction was performed at room temperature, under anaerobic condition for 6-8 hours. After reaction completion, the solvent was evaporated under reduced pressure. The residue was dissolved in ethyl acetate and washed with saturated aqueous $CuSO_4$ solution. The organic phase was separated and 0.5 g of $Na_2SO_4$ per gram of TEMPOL was added to the organic phase. The solution was mixed for 15 min at room temperature followed by filtration. Filtered solution was evaporated under reduced pressure. The product, 4-Succinimidyl-TEMPO-Carbonate, was precipitated by adding n-heptane, filtered, and dried under vacuum at room temperature.

A reaction scheme for the preparation of 4-Succinimidyl-TEMPO-Carbonate is shown below:

Example 2. Analysis of 4-Succinimidyl-TEMPO-Carbonate (4-STC)

Figure 2:
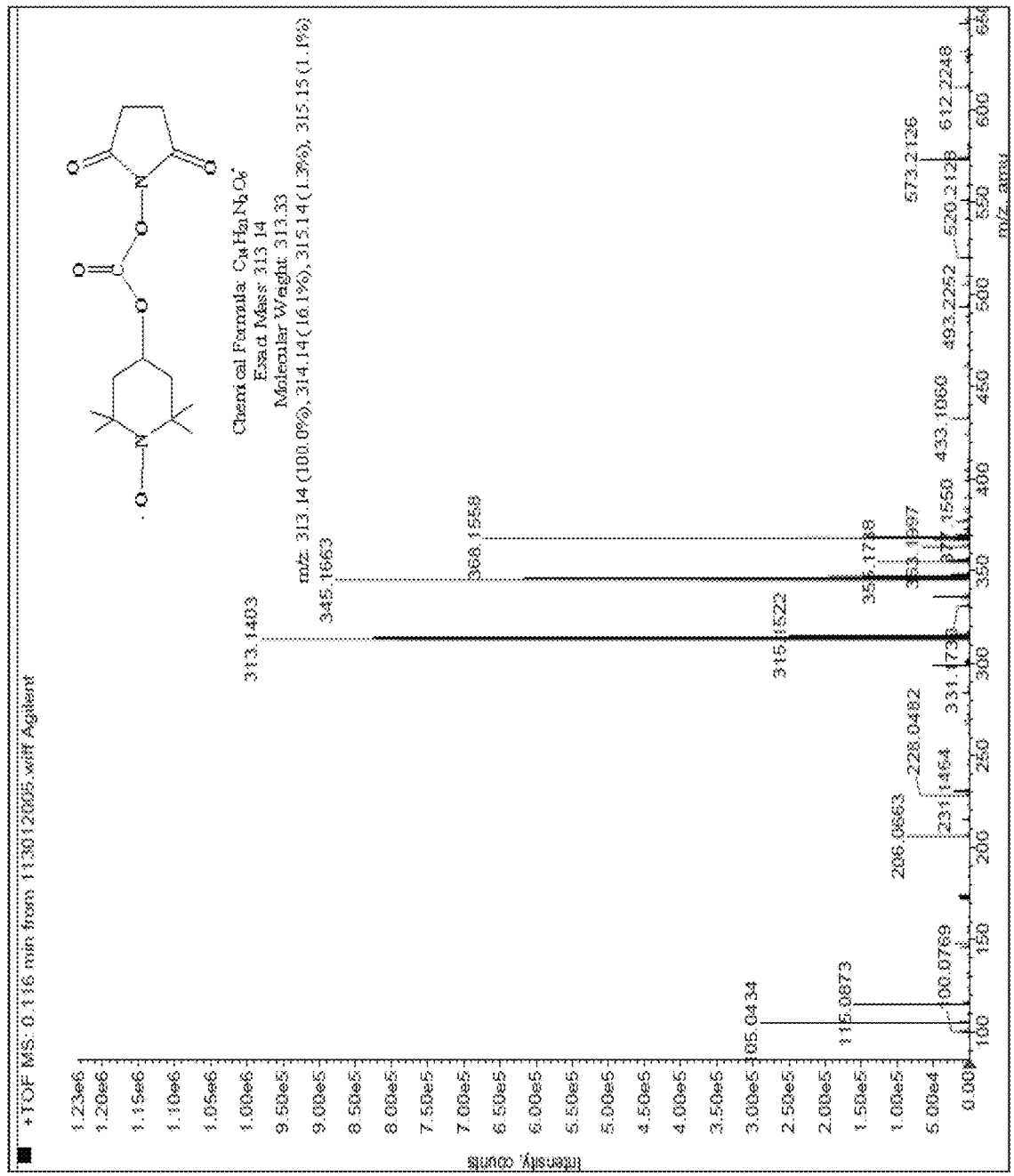
FIG. 2 shows the results of ESI-TOF high accuracy mass spectroscopy confirming the molecular structure of 4-Succinimidyl-TEMPO-Carbonate (4-STC).

ESI-TOF high accuracy mass spectroscopy was performed on the starting material TEMPOL and the final product 4-Succinimidyl-TEMPO-Carbonate (4-STC) to confirm conversion of TEMPOL to 4-STC (FIGS. 1 and 2).

Figure 3:
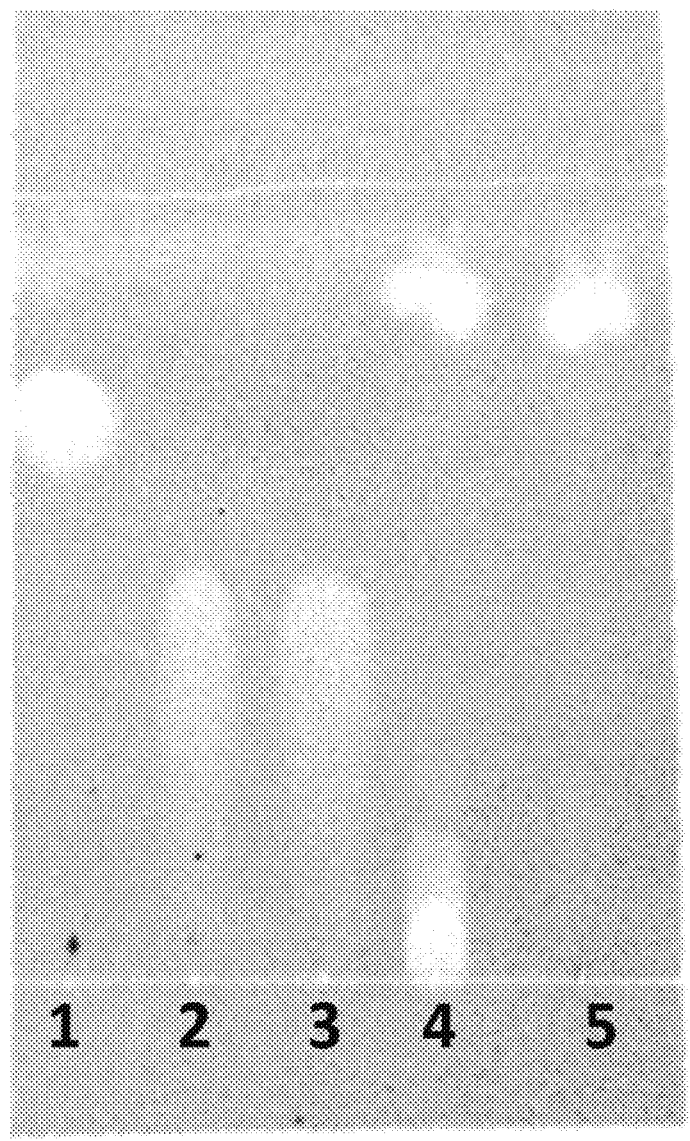
FIG. 3 shows thin layer chromatography (TLC) results performed on TEMPOL, N'-Disuccinimidyl carbonate (DSC), N-hydroxy-succinimide (NHS), reaction products from the reaction of TEMPOL and DSC at a 6 hour timepoint, and the final 4-STC reaction product.

In addition, as shown in FIG. 3 thin layer chromatography was performed on the starting materials TEMPOL (lane 1) and N,N'-Disuccinimidyl carbonate (DSC, lane 3), and the reaction product at 6 hours (lane 4) and the final product 4-Succinimidyl-TEMPO-Carbonate after precipitation (lane 5). Lane 2 was loaded with N-hydroxy-succinimide (NHS), a reaction by-product that is released from DSC during the reaction. As can be seen from FIG. 3, the final product does not contain any of the starting materials or by-products.

Example 3. Synthesis of 3-Succinimidyl-PROXYL-Carbonate (3-SPC;1-(((2,2,5,5-tetramethyl-1-pyrrolidinyloxy)-3-oxycarbonyl)oxy)-2,5-pyrrolidinedione)

3-Succinimidyl-PROXYL-Carbonate can be prepared using a method similar to those described above in Example 1 for 4-Succinimidyl-TEMPO-Carbonate, using 3-hydroxy-2,2,5,5-tetramethylpyrrolidin-1-oxyl instead of TEMPOL as a starting material.

Example 4. Synthesis of 4-succinimidyl-carboxy-TEMPO (4-SCT; 1-(((2,2,6,6-tetramethyl-1-piperidinyloxy)-4-carbonyl)oxy)-2,5-pyrrolidinedione)

One gram of 4-Carboxy-2,2,6,6-tetramethylpiperidin-1-oxyl (4-Carboxy TEMPO) was dissolved in 75 mL tetrahydrofuran and mixed for five minutes at room temperature. Once the 4-Carboxy TEMPO dissolved, 0.632 g of N-Hydroxysuccinimide (NHS) (1.1 eq) and 1.15 g of N,N'-Dicyclohexylcarbodiimide (1.1 eq) were added to the reaction. The reaction was performed at room temperature under anaerobic conditions for 24 hours. After reaction completion, the solution was filtered and evaporated under reduced pressure. The residue was dissolved in ethyl acetate and washed with water. The organic phase was separated and 0.5 g of $Na_2SO_4$ per gram of 4-Carboxy TEMPO was added to the organic phase. The solution was mixed for 15 min at room temperature followed by filtration. Filtered solution was evaporated under the reduced pressure. The product,

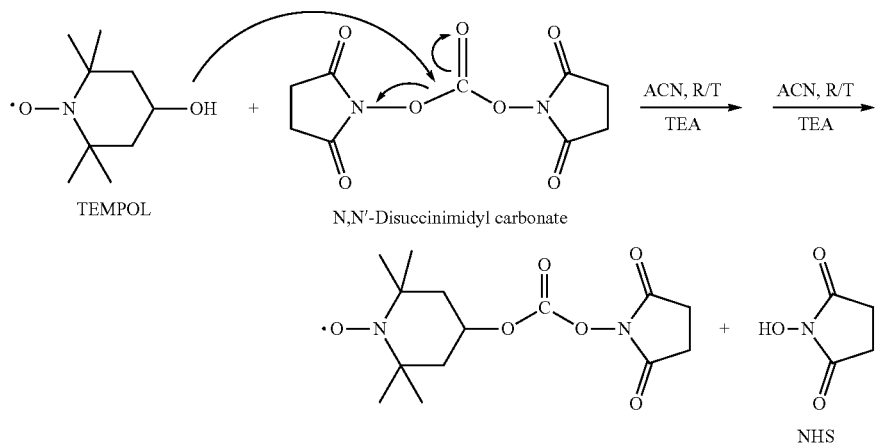

4-Succinimidyl-Carboxy-TEMPO was precipitated by adding n-Heptane, filtered, and dried under vacuum at room temperature.

A reaction scheme for the preparation of 4-Succinimidyl-Carboxy-TEMPO is shown below:

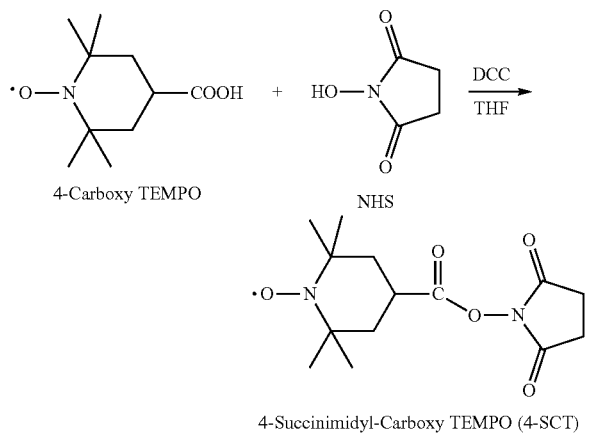

4-Succinimidyl-Carboxy TEMPO (4-SCT)

Example 5. Synthesis of 3-Succinimidyl-Carboxy-PROXYL (3-SCP; 1-(((2,2,5,5-tetramethyl-1-pyrrolidinyloxy)-3-carbonyl)oxy-2,5-pyrrolidinedione)

3-Succinimidyl-Carboxy Proxyl can be synthesized using the same chemistry as described above in Example 3 for 4-Succinimidyl-Carboxy-TEMPO, using 3-carboxy-2,2,5,5-tetramethylpyrrolidin-1-oxyl (3-Carboxy PROXYL) instead of 4-Carboxy TEMPO as a starting material.

Example 6. Preparation of polynitroxylated PEGylated hemoglobin (PN-PEG-Hb)

Polynitoxylated hemoglobin was prepared in two step process: a) Preparation of PEG-conjugated hemoglobin and b) Polynitoxylation of PEG-Hb.

PEG was conjugated to stroma-free hemoglobin (SFH) by reacting the SFH with a 9-fold molar excess of 2-iminothiolane (2-IT) for 2.5 hours and a 16-fold molar excess of Maleimide PEG 5000 (MalPEG5000) for 2 hours. The thiolation and PEGylation reactions were performed in phosphate-buffered saline (PBS) at pH 7.4. As shown in the reaction scheme below, the 2-iminothiolane thiolates lysine residues and the MalPEG5000 reacts with intrinsic thiols of the β-Cys93 residues and thiolated lysine residues:

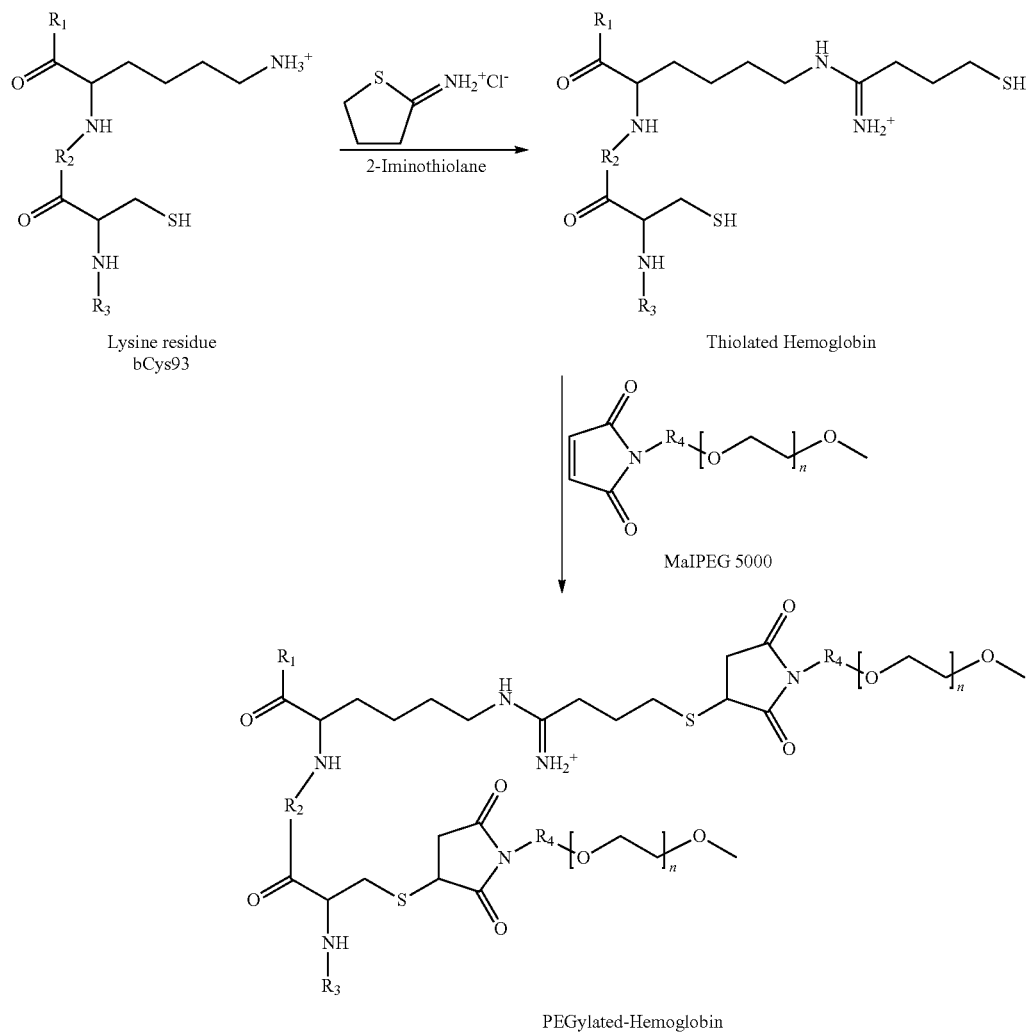

$R_1$, $R_2$, and $R_3$ represent the remainder of the hemoglobin main chain, $R_4$ is ethylene, and n represents the number of oxyethylene units in a 5,000 dalton PEG chain. Although the reaction scheme above shows the thiolation and PEGylation as separate steps, the reaction is performed as a "one-pot" reaction, with the SFH, 2-IT, and MalPEG 5000 included in a single reaction mixture.

Polynitroxylation of the PEG-Hb was performed using carboxy-PEG-Hb. The reaction was performed using a 30-fold molar excess of 4-Succinimidyl-TEMPO-Carbonate (4-STC) over hemoglobin under an atmosphere of CO at room temperature or in refrigerated conditions. The number of nitroxyl groups per hemoglobin molecule can be varied by varying the molar excess of 4-STC over hemoglobin, the temperature at which the reaction is carried out, and/or reaction time. The polynitroxylated hemoglobin was purified using 70 kDa tangential flow filtration and the final product was sterile filtered and stored under an atmosphere of CO. A reaction scheme for the preparation of PN-PEG-Hb from PEG-Hb is shown below:

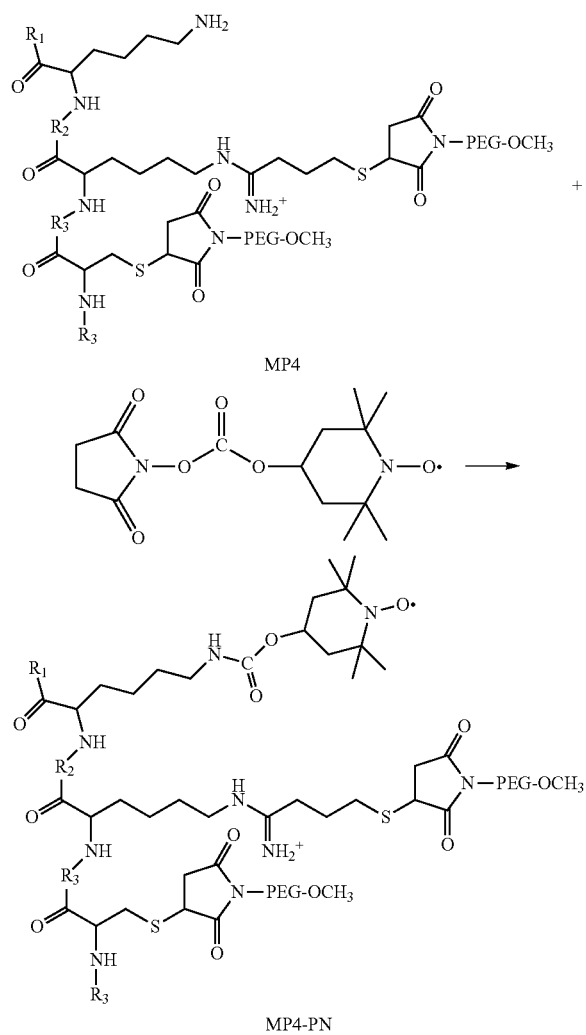

$R_1$, $R_2$, and $R_3$ represent the remainder of the hemoglobin main chain.

Example 7. Characterization of polynitroxylated PEGylated hemoglobin (PN-PEG-Hb)

Figure 4:
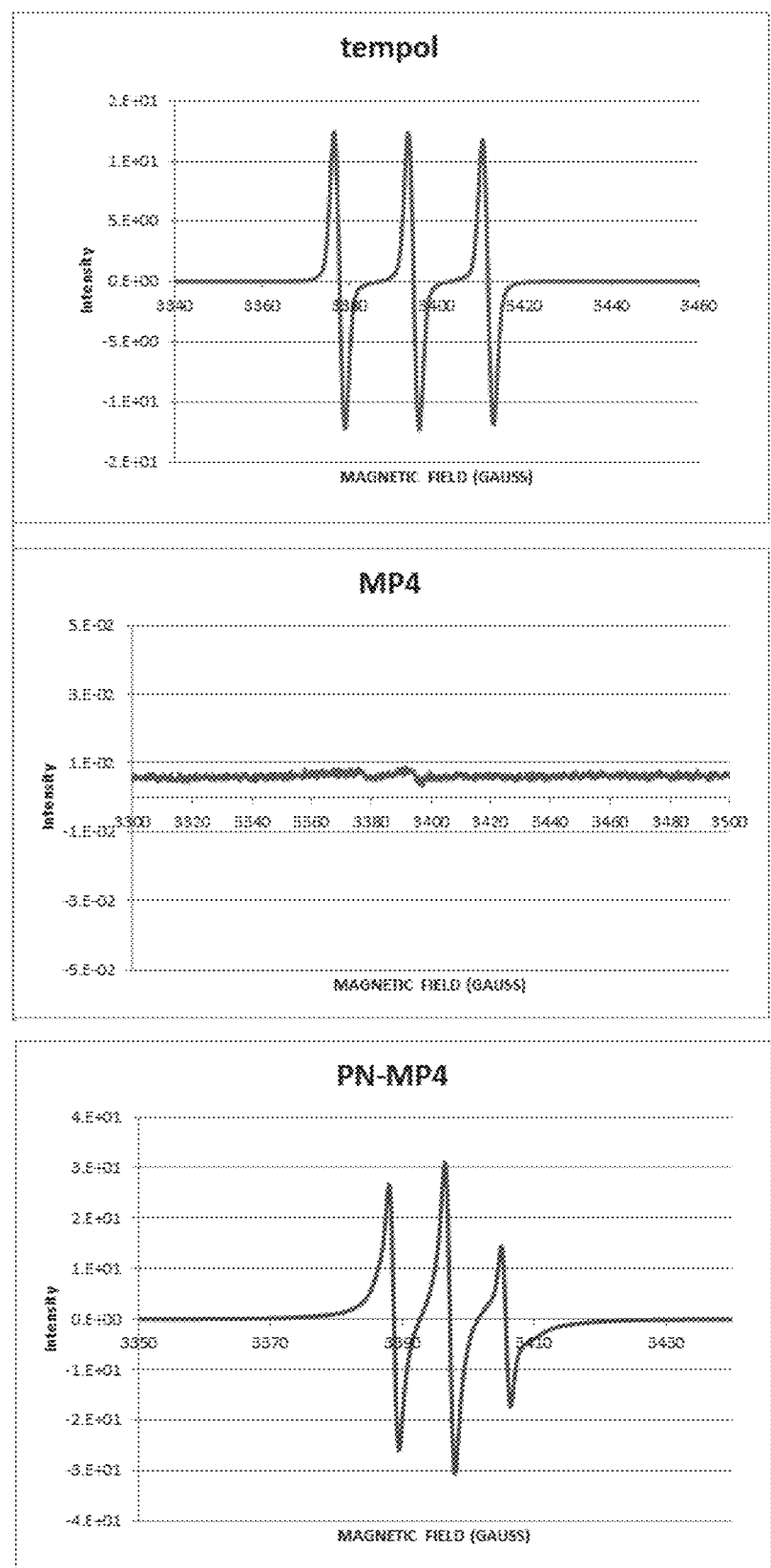
FIG. 4 shows Electron Paramagnetic Resonance (EPR) spectra for TEMPOL and PEGylated hemoglobin (MP4) both before and after polynitroxylation (PN-MP4).

FIG. 4 shows Electron Paramagnetic Resonance (EPR) spectra for non-paired electrons of TEMPOL (upper panel), and PEGylated hemoglobin (MP4) both before (middle panel) and after (lower panel) polynitroxylation (PN-MP4).

Figure 5:
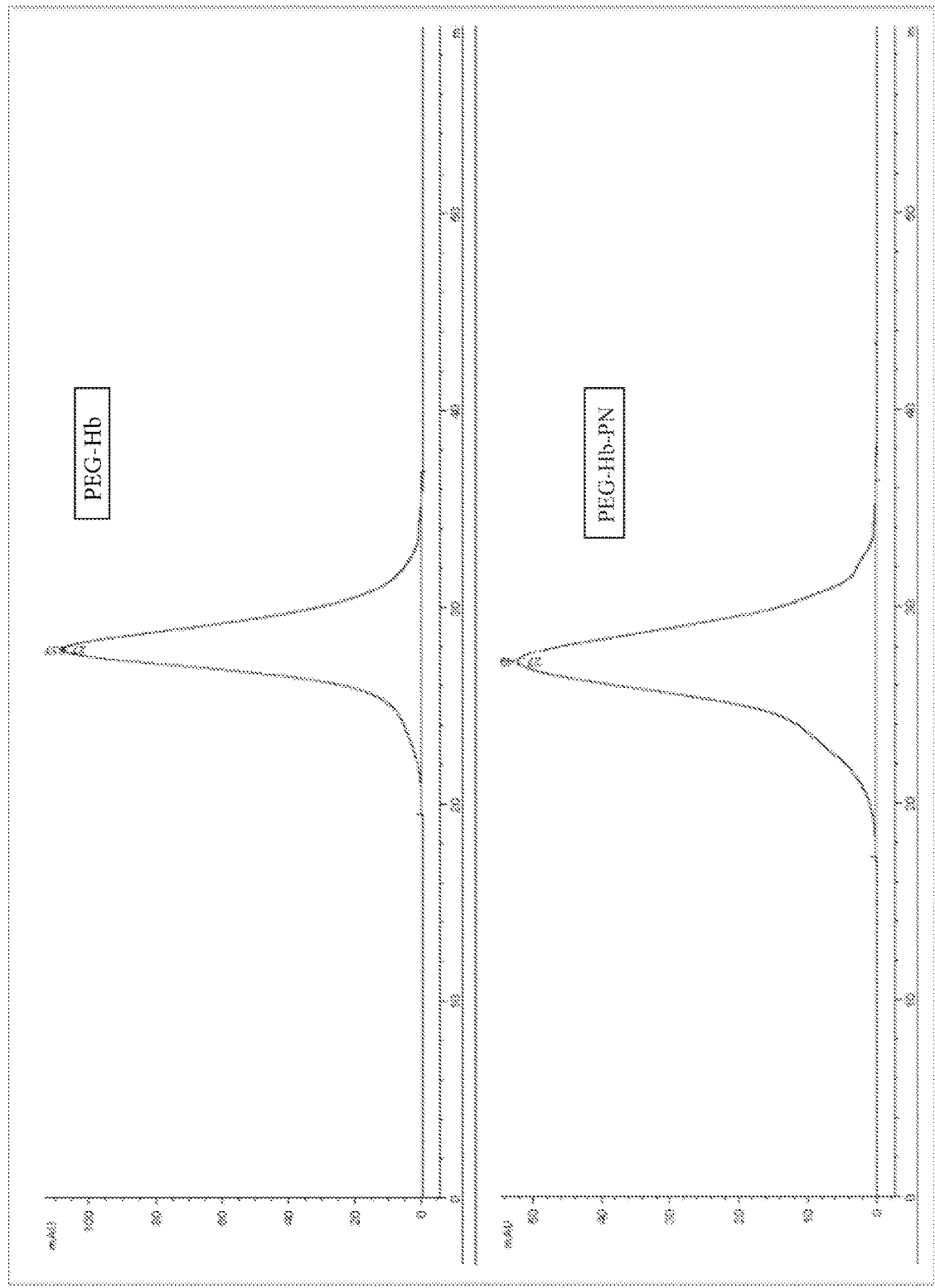
FIG. 5 shows a size exclusion analysis profiles of PEGylated hemoglobin (PEG-Hb) and polynitroxylated PEGylated hemoglobin (PEG-Hb-PN).

FIG. 5 presents size exclusion analysis profiles of PEGylated hemoglobin (PEG-Hb; upper panel) and polynitroxylated PEGylated hemoglobin (PEG-Hb-PN; lower panel). Size exclusion analysis was performed using a Superose-12 column and protein was eluted using phosphate-buffered saline (PBS).

Figure 6:
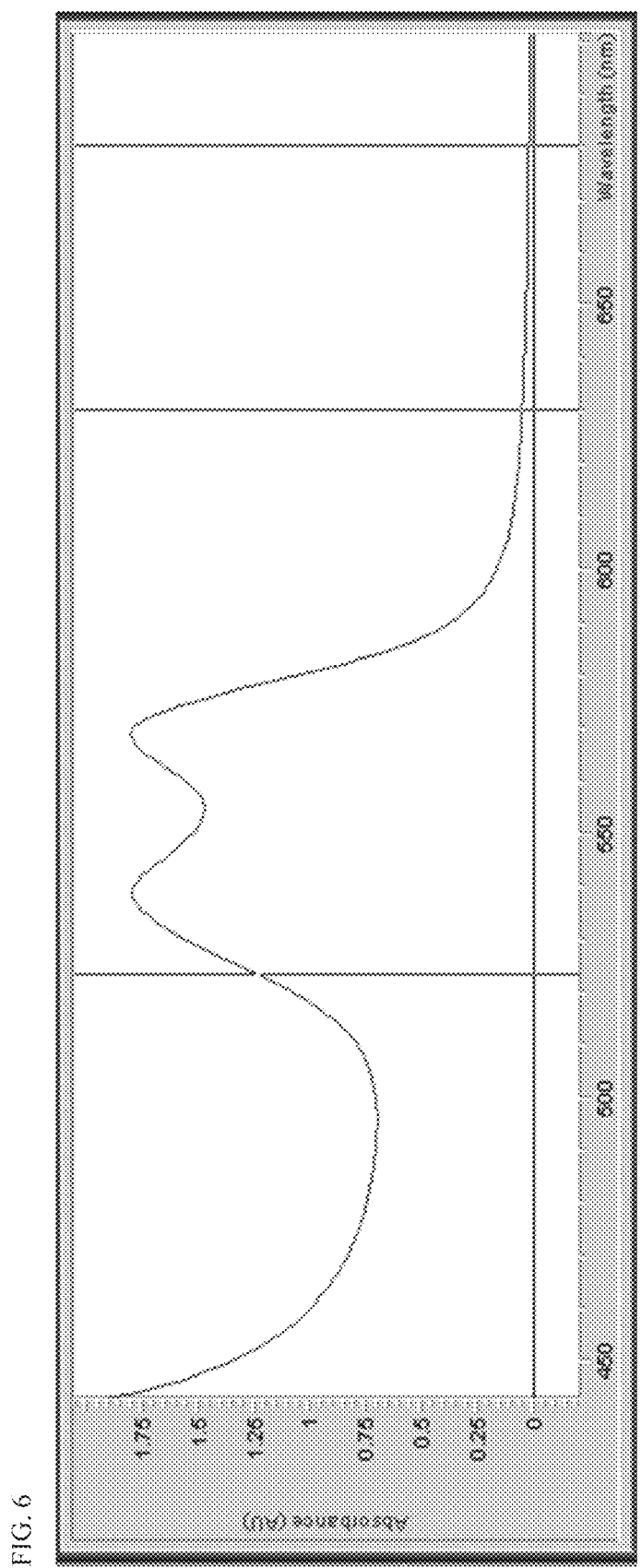
FIG. 6 shows a characteristic UV-Vis spectrum for polynitroxylated PEGylated hemoglobin (PEG-Hb-PN).

FIG. 6 shows a characteristic UV-Visible spectrum for polynitroxylated PEGylated hemoglobin (PEG-Hb-PN).

Figure 7:
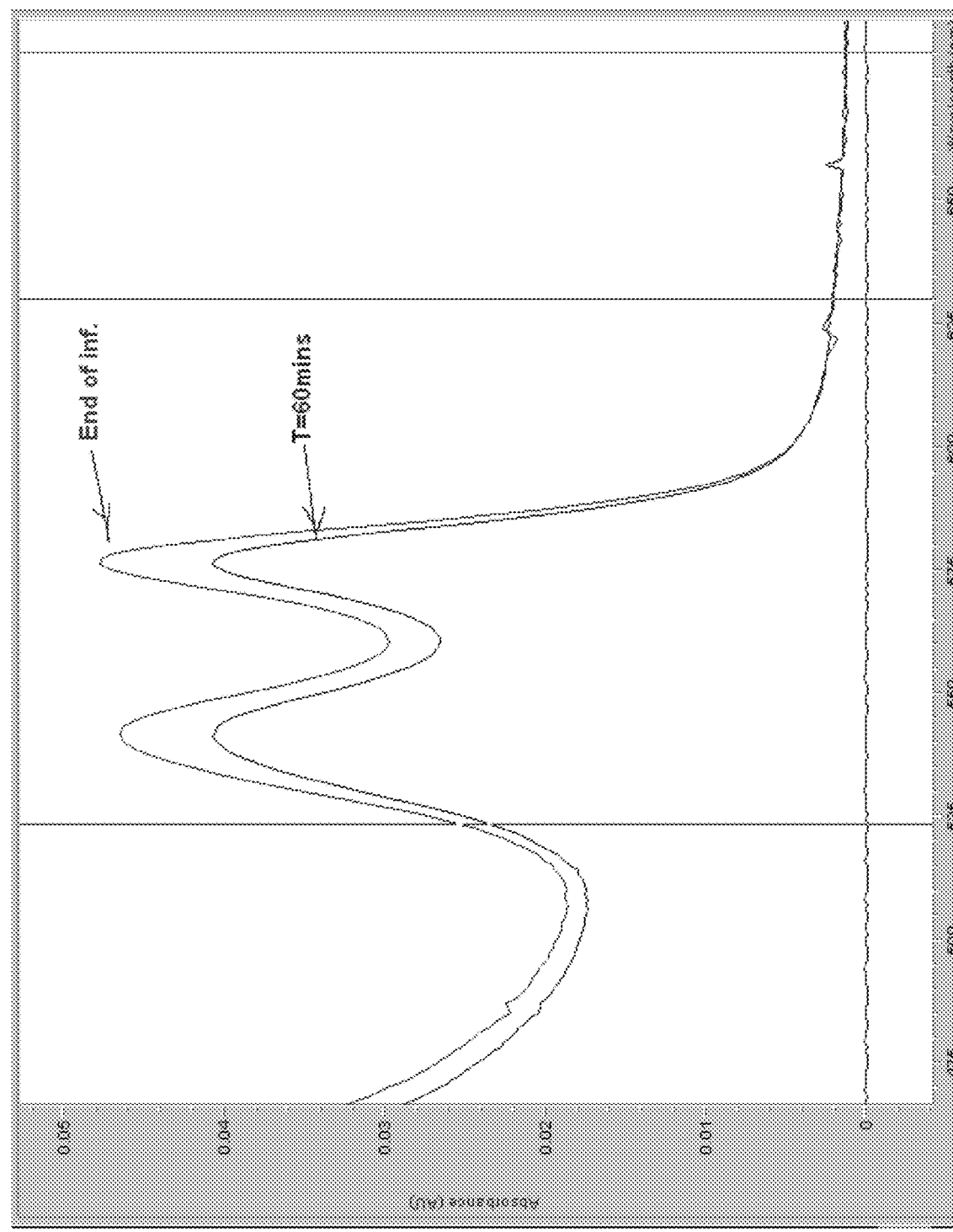
FIG. 7 shows UV-Vis spectra for plasma hemoglobin following administration of PEG-Hb-PN to rats.

The stability of the PEG-Hb-PN was tested in vivo by administering 10% top load in rats. FIG. 7 shows UV-Vis spectra of plasma hemoglobin at the end of infusion and at one hour post infusion.

Figure 8:
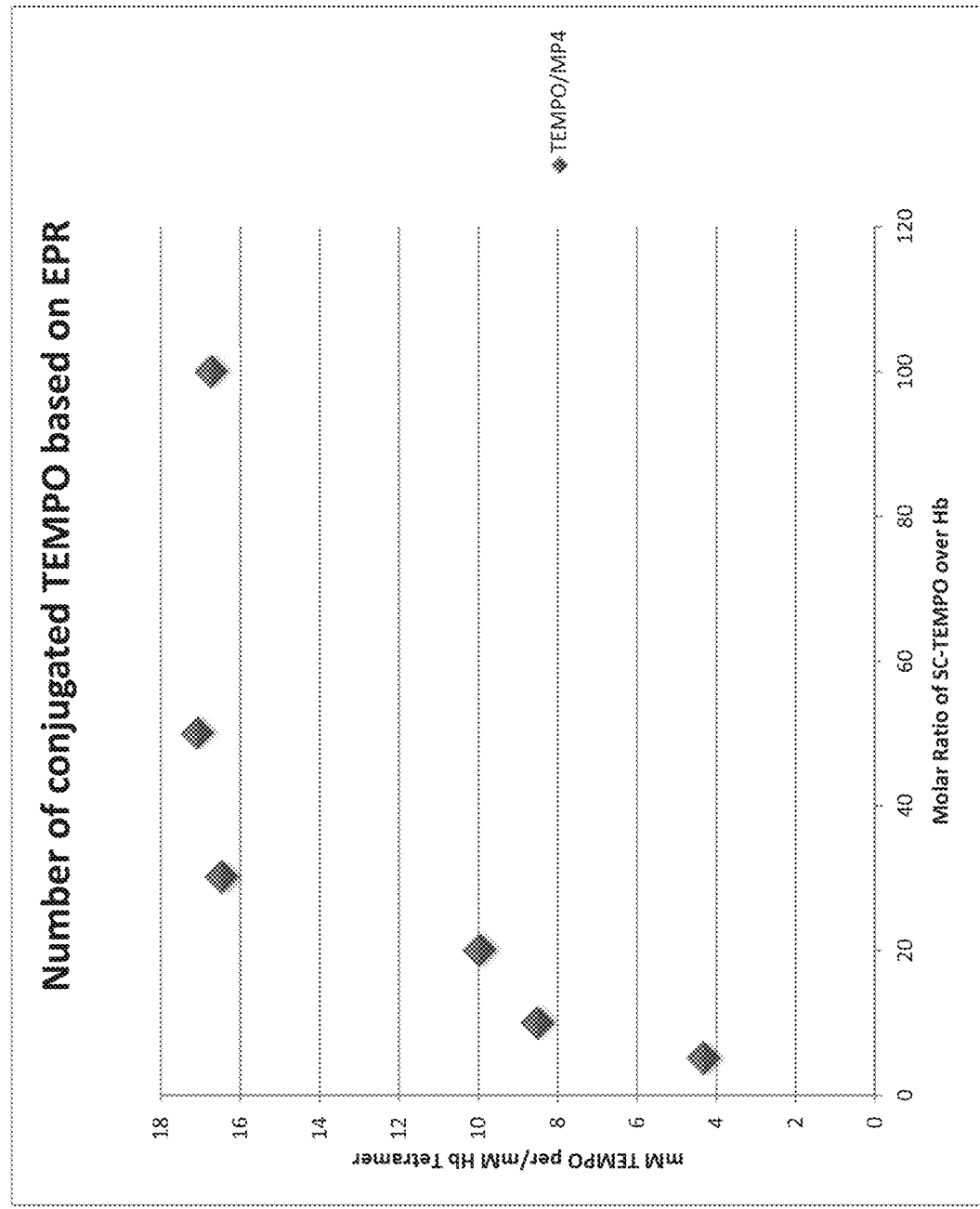
FIG. 8 shows representative results of an experiment wherein PEGylated hemoglobin was nitroxylated using 4-Succinimidyl-TEMPO-Carbonate (4-STC) at a molar excess of 1:5-1:100 over the PEGylated hemoglobin.

FIG. 8 shows the results of an experiment wherein PEGylated hemoglobin (MP4) was nitroxylated using a 5-, 10-, 20, 30-, 50-, or 100-fold molar excess of 4-Succinimidyl-TEMPO-Carbonate (4-STC). The degree of nitroxylation increased in a dose-dependent manner as the molar excess of 4-STC was increased from 5-fold to 30-fold. The degree of nitroxylation was approximately the same when a 30-fold, 50-fold, or 100-fold molar excess of 4-STC was used.

Example 8. Preparation of Polynitroxylated Albumin (PN-Alb)

Polynitroxylation of the Albumin was performed using 25% Human Serum Albumin solution. The number of nitroxyl groups per albumin molecule was varied by varying the molar excess of 4-STC over albumin. The reaction was performed using a 5-, 10-, 20-, 30-, 50 or 100-fold molar excess of 4-Succinimidyl-TEMPO-Carbonate (4-STC) over albumin at pH of 7.4 for 17 to 24 hours at room temperature or in refrigerated conditions. The polynitroxylated albumin was purified by gel filtration and analyzed by MALDI-TOF mass spectrometry to identify the number of nitroxyl groups per albumin molecule. A reaction scheme for the preparation of PN-Albumin from albumin using 4-Succinimidyl-TEMPO-Carbonate (4-STC) is shown below:

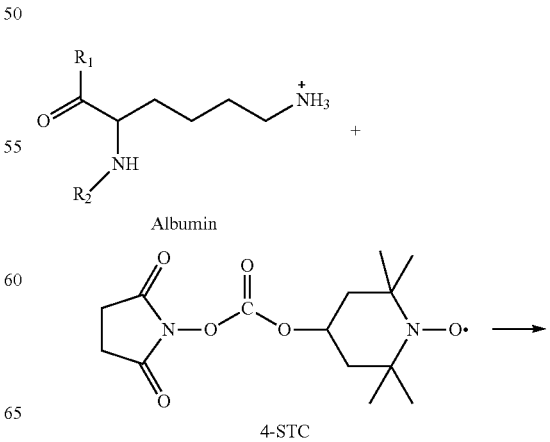

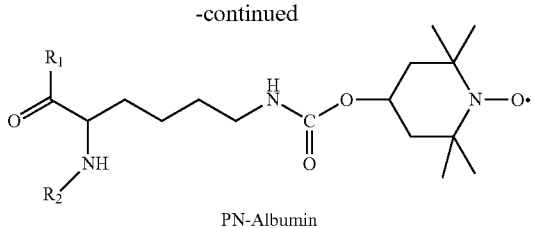

PN-Albumin $R_1$ and $R_2$ represent the remainder of the albumin main chain.

Figure 9:
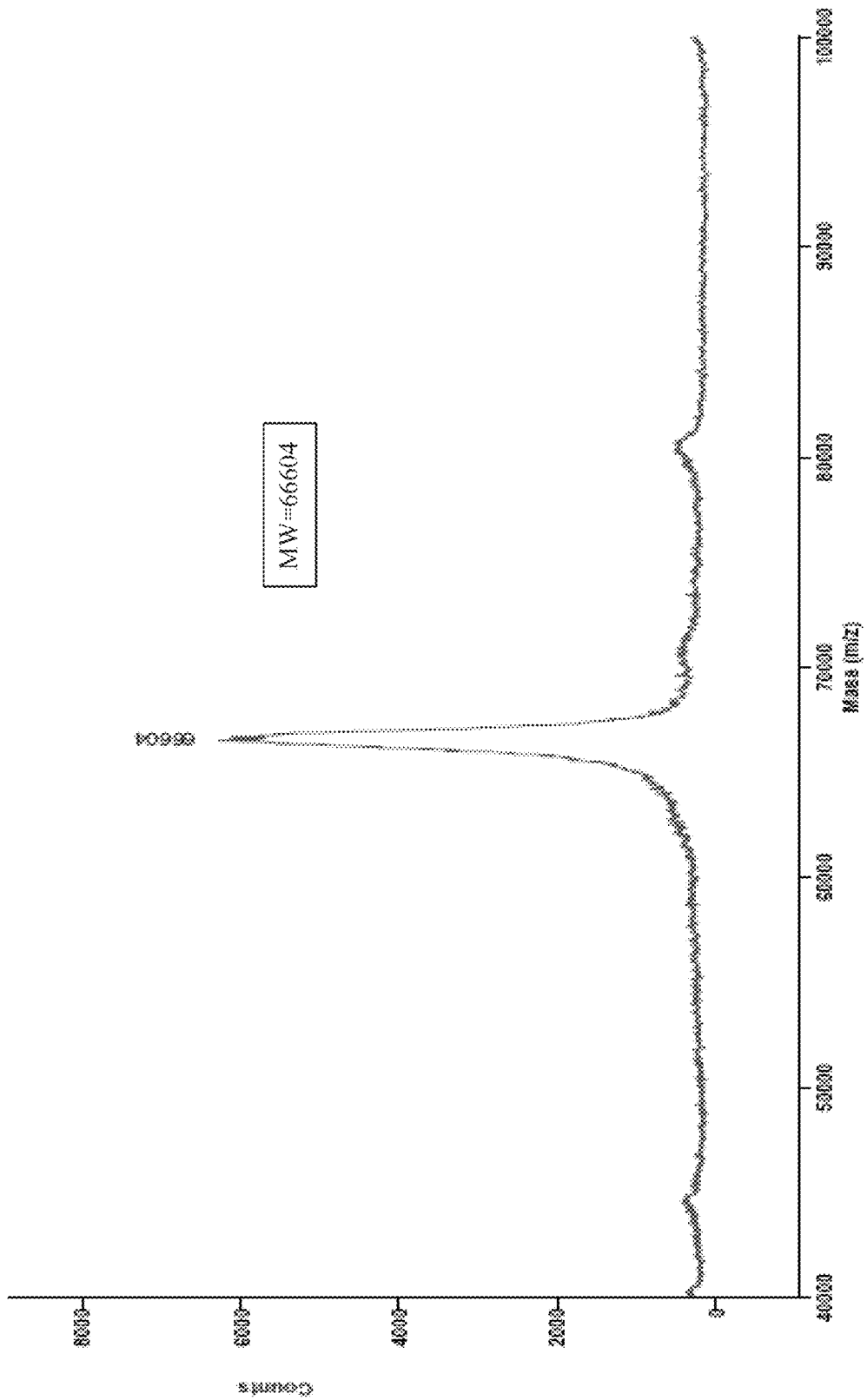
FIGS. 9 and 13 show MALDI-TOF spectra for human serum albumin (HSA).
Figure 10:
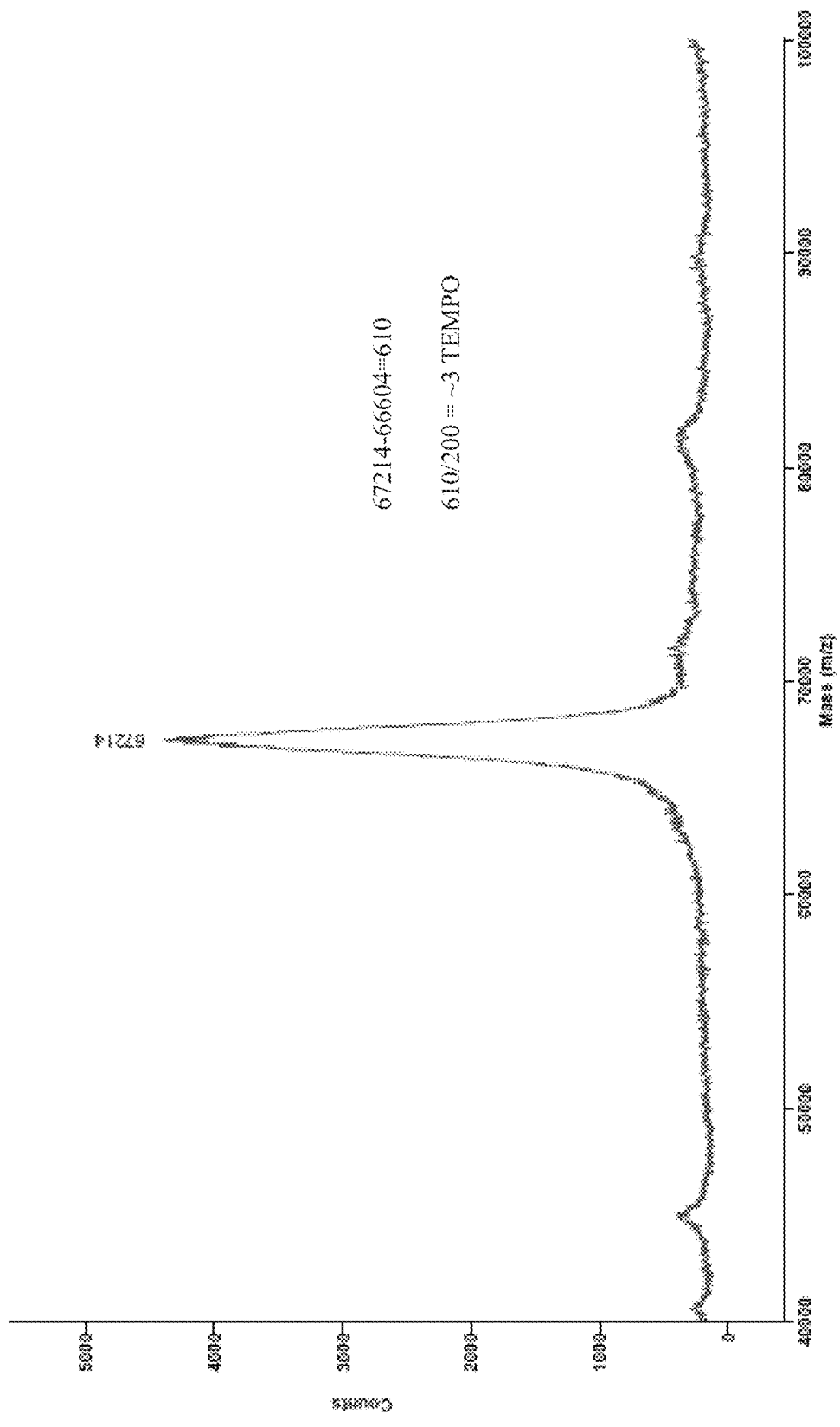
FIGS. 10-12 and 14-16 show MALDI-TOF spectra for HSA polynitroxylated using 4-Succinimidyl-TEMPO-Carbonate at a molar excess of 1:5-1:100 over HSA.
Figure 11:
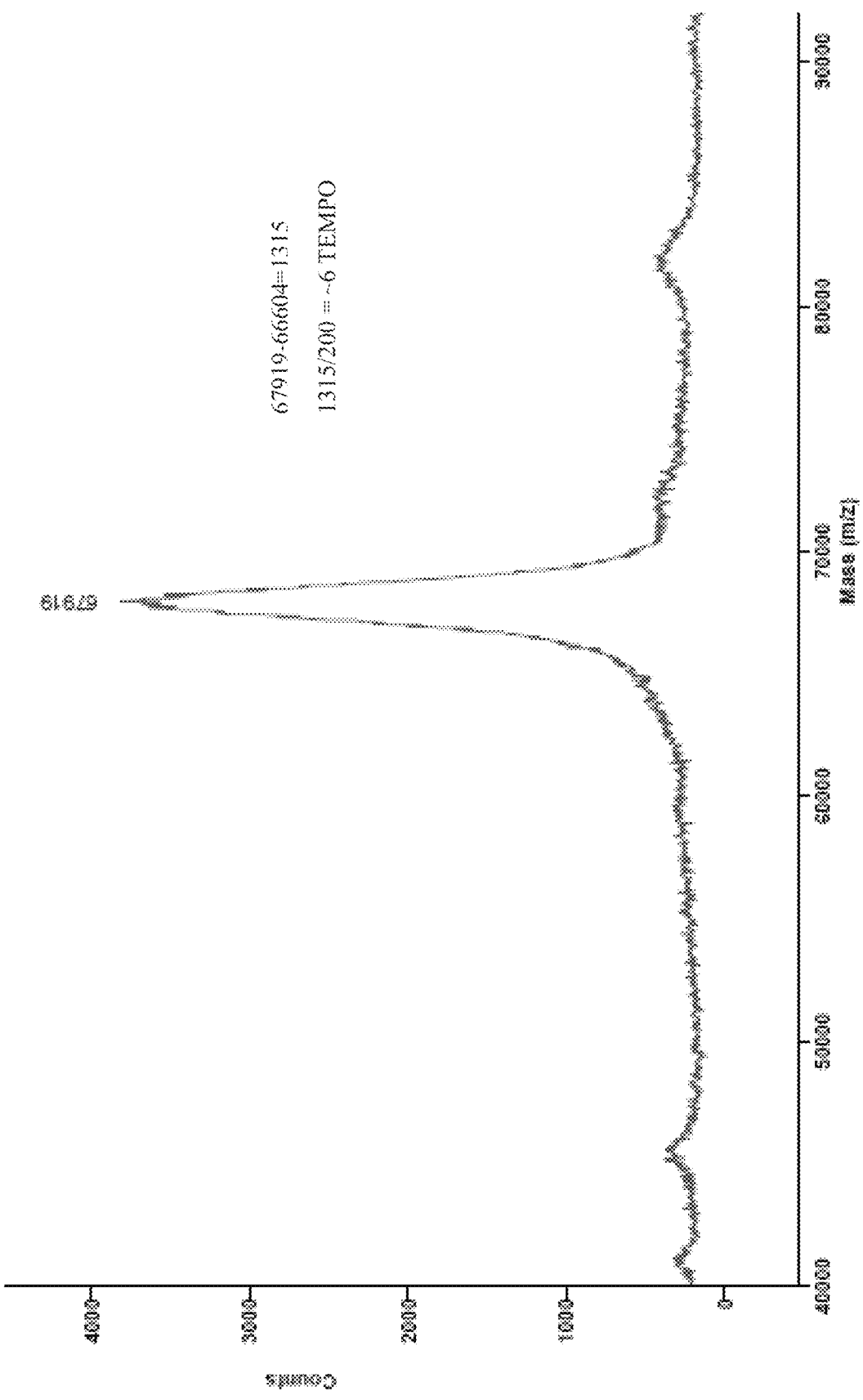
Figure 12:
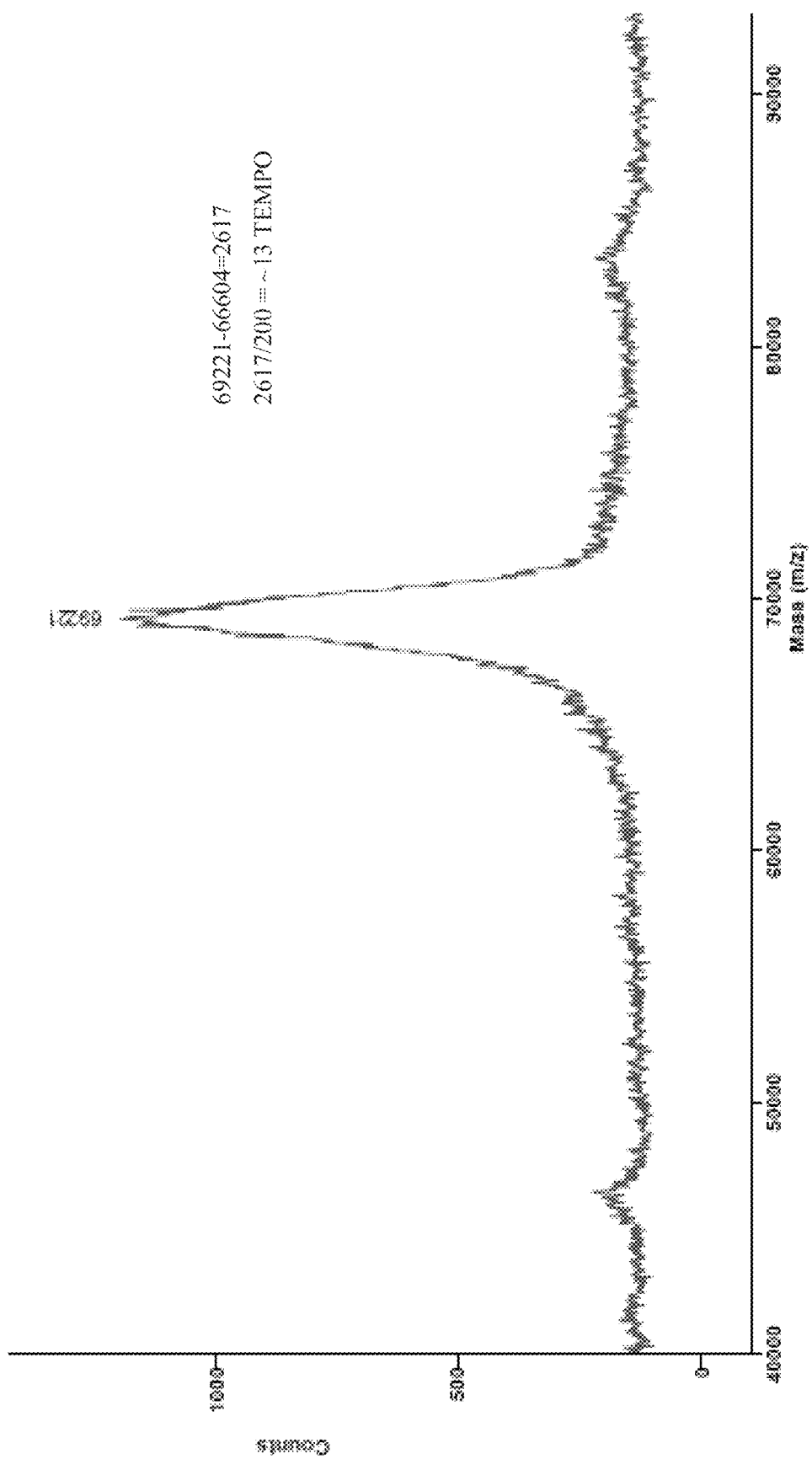
Figure 13:
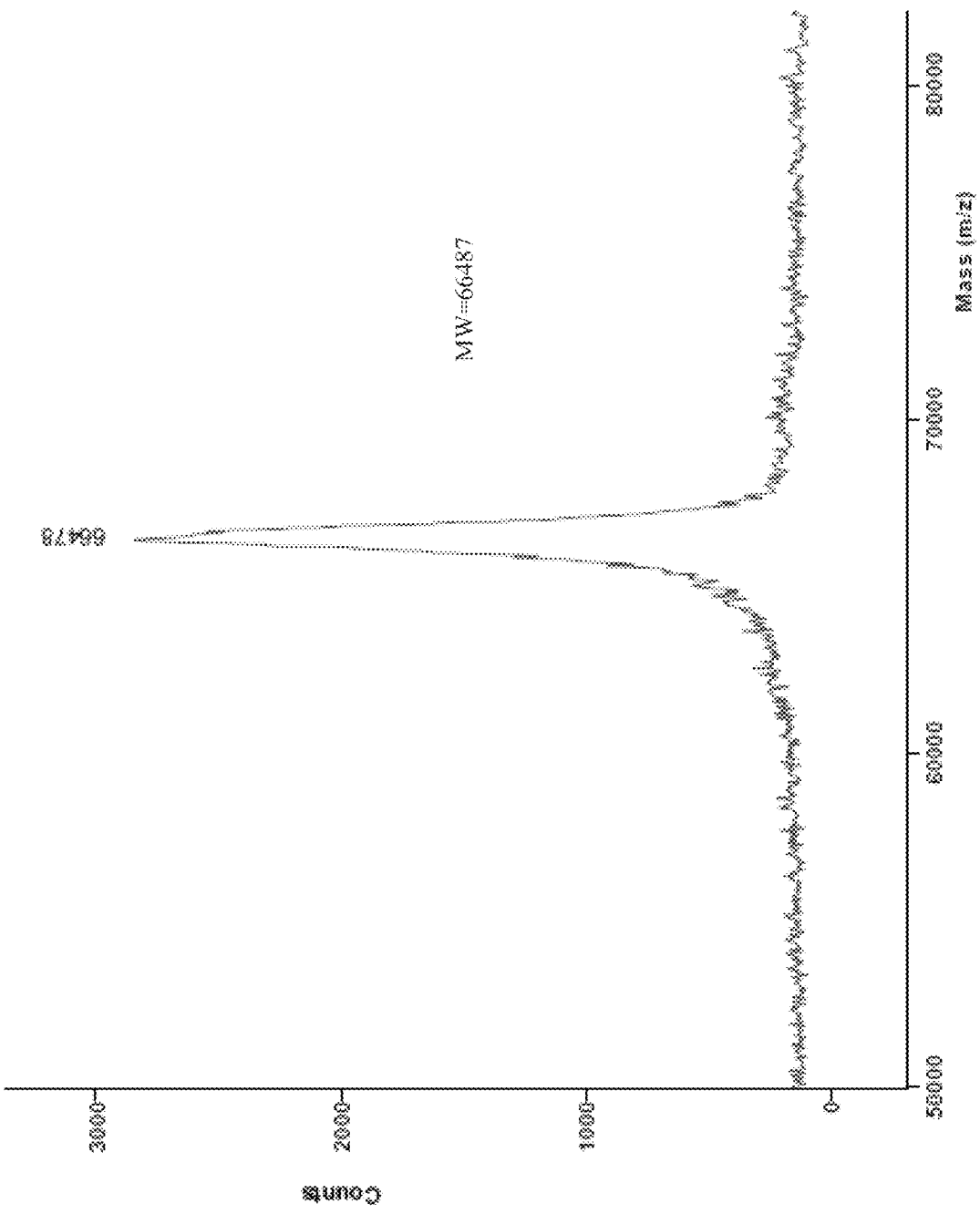
Figure 14:
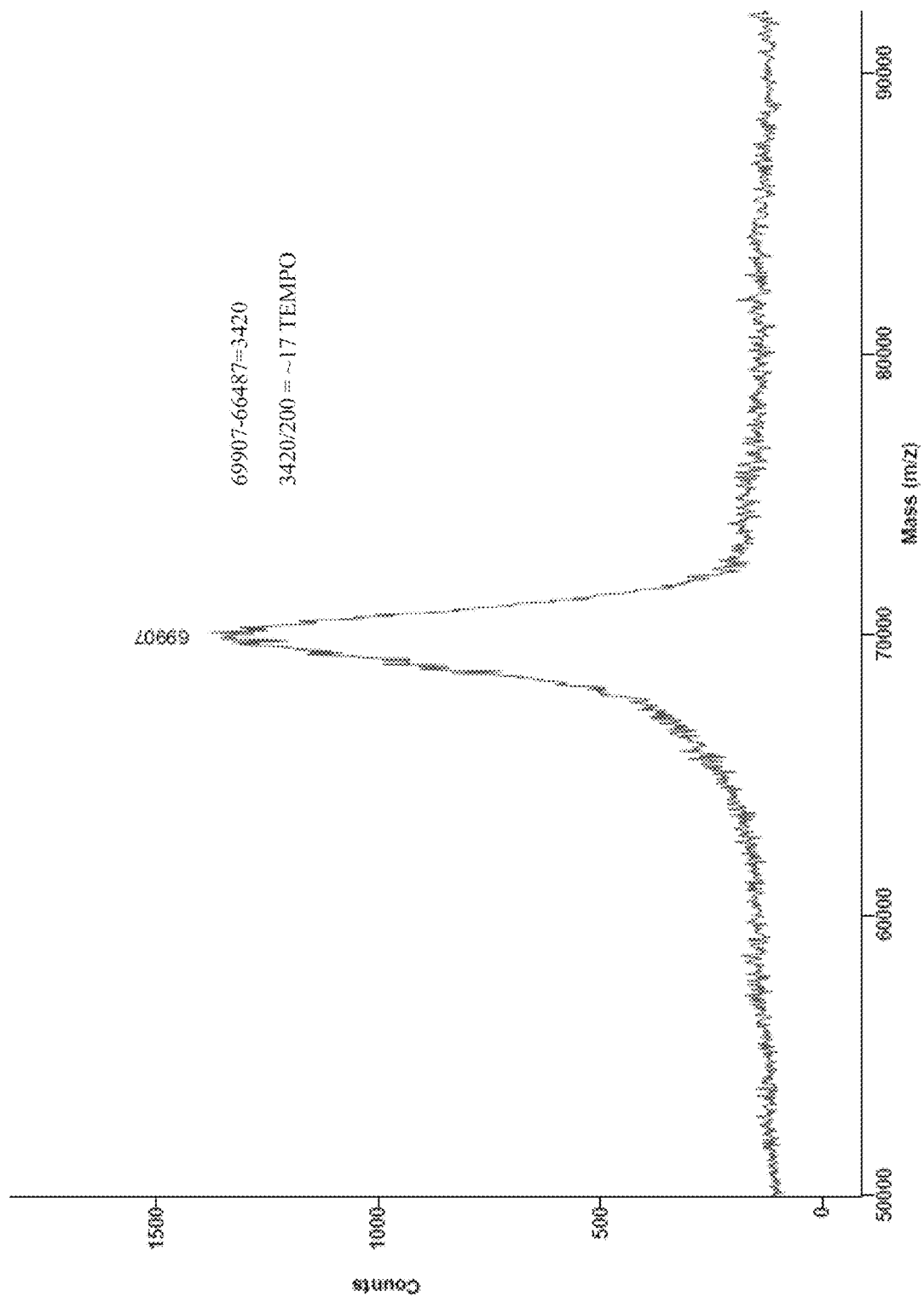
Figure 15:
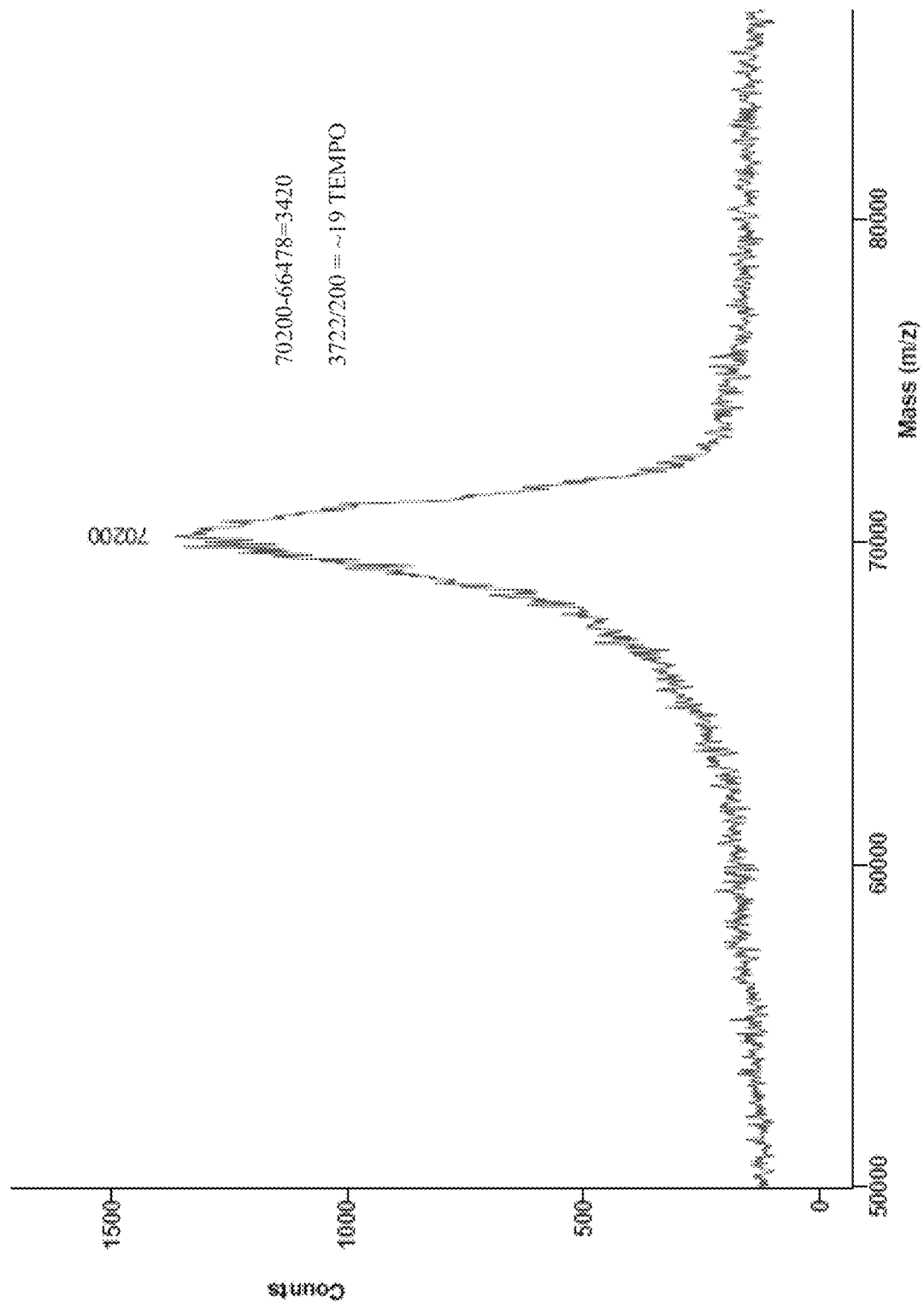
Figure 16:
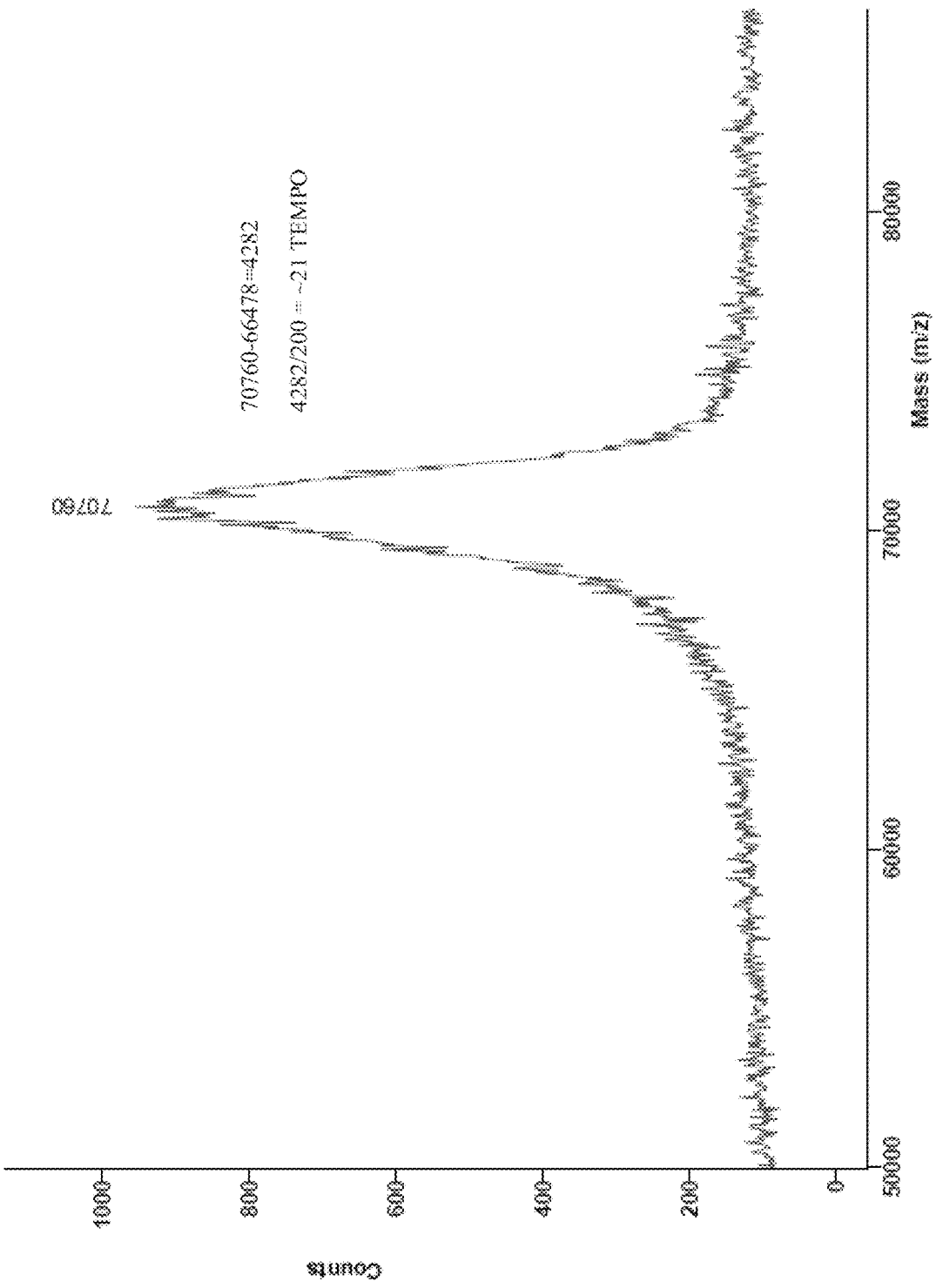

The MALDI-TOF mass spectra are shown in FIGS. 9 and 13 (non-nitoxylated HSA) and 10-12 and 14-16 (HSA nitroxylated using a 5-, 10-, 20-, 30-, 50 or 100-fold molar excess of 4-STC, respectively). FIG. 17 provides a graphical representation of these data, and shows that the degree of nitroxylation increased in a dose-dependent manner as the molar excess of 4-STC was increased from 5- to 100-fold.

Example 9. Preparation of polynitroxylated PEGylated-Albumin (PN-PEG-Alb)

Polynitoxylated PEGylated albumin was prepared in two step process: a) Preparation of PEG-conjugated albumin and b) Polynitoxylation of PEG-Alb.

PEG was conjugated to albumin by reacting the albumin with a 9-fold molar excess of 2-iminothiolane (2-IT) for 2.5 hours and a 16-fold molar excess of Maleimide PEG 5000 (MalPEG5000) for 2 hours. The thiolation and PEGylation reactions were performed in phosphate-buffered saline (PBS) at pH 7.4. After the 2 hours of PEGylation, the PEG-albumin conjugate was passed through 70 kDa tangential flow filtration to remove unreacted reagents and formulate in formulation buffer. Polynitroxylation was performed by reacting PEG-albumin with 4-Succinimidyl-TEMPO-Carbonate (4-STC) using a 100-fold molar excess of 4-Succinimidyl-TEMPO-Carbonate (4-STC) over albumin at room temperature or in refrigerated conditions. The number of nitroxyl groups per albumin molecule can be varied by varying the molar excess of 4-STC over albumin, the temperature at which the reaction is carried out, and/or reaction time. The polynitroxylated albumin was purified using 70 kDa tangential flow filtration. A reaction scheme for the preparation of PN-PEG-Alb from PEG-Alb is shown below:

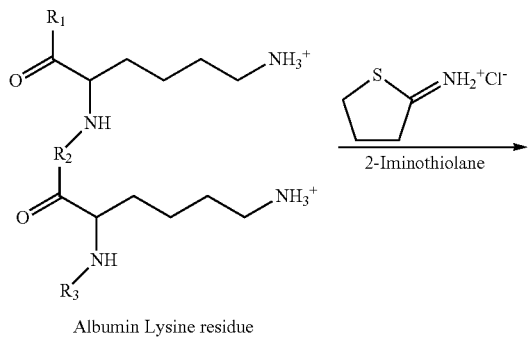

Albumin Lysine residue

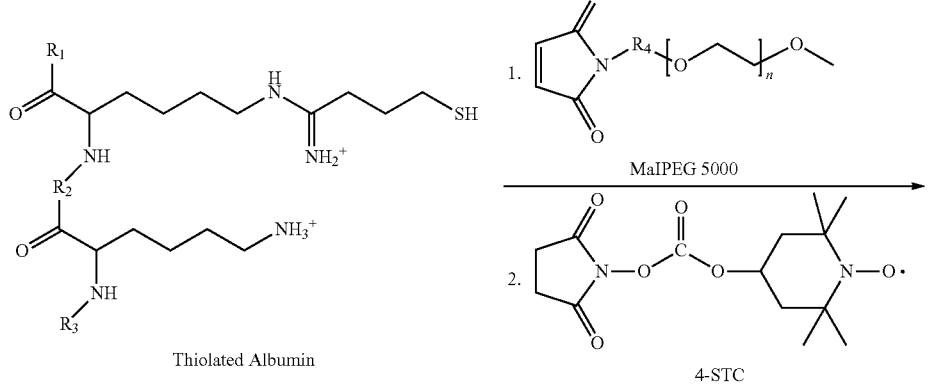

Thiolated Albumin

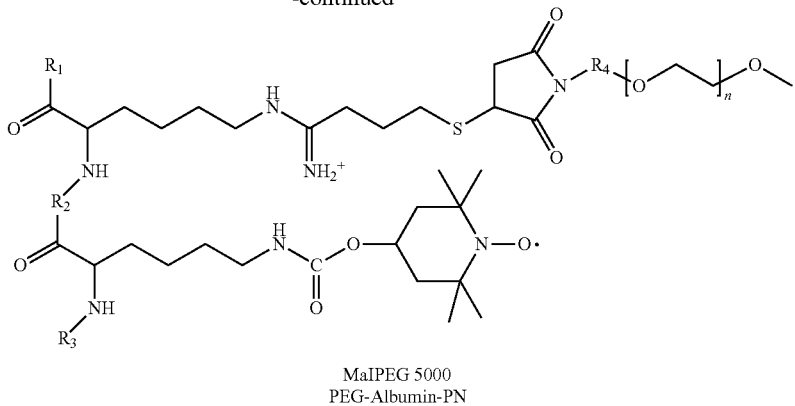

MaIPEG 5000
PEG-Albumin-PN $R_1$, $R_2$, and $R_3$ represent the remainder of the albumin main chain, $R_4$ is ethylene, and n represents the number of oxyethylene units in a 5,000 dalton PEG chain.

What is claimed is:

1. A method for preparing a nitroxylated protein comprising reacting the protein with a nitroxylating agent of formula (I):

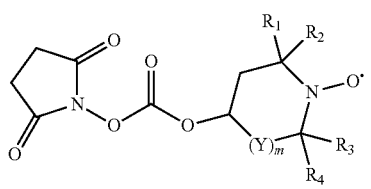

wherein
each of $R_1$, $R_2$, $R_3$, and $R_4$ is independently $C_1$-$C_4$ alkyl;
Y is $CH_2$;
and
m is 0 or 1,
wherein reacting the protein with the nitroxylating agent results in nitroxylation of an N-terminal amino group of the protein or at least one epsilon (ε)-amino group of a lysine residue of the protein; and the nitroxylated protein has the structure (VI):

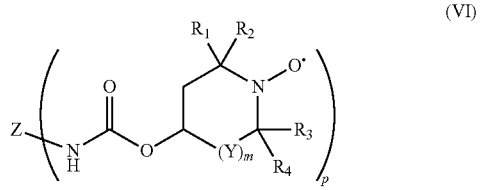

wherein
Z represents the protein, and the protein comprises a hemoglobin tetramer;
each of $R_1$, $R_2$, $R_3$, and $R_4$ are independently $C_1$-$C_4$ alkyl;
Y is $CH_2$;
m is 0 or 1;
p is the average number of nitroxyl groups conjugated to the protein; and
N is a nitrogen of the protein.

2. The method of claim 1, wherein each of $R_1$, $R_2$, $R_3$, and $R_4$ is —$CH_3$.

3. The method of claim 1, wherein m is 1.

4. The method of claim 1, wherein reacting the protein with the nitroxylating agent results in conjugation of about 1 to about 25 nitroxyl groups to the protein.

5. The method of claim 1, wherein the hemoglobin tetramer comprises a cross-linked αα dimer or a cross-linked ββ dimer.

6. The method of claim 1, wherein reacting the hemoglobin tetramer with the nitroxylating agent results in about seventeen nitroxylated amino groups on the hemoglobin tetramer.

7. The method of claim 1, wherein the method further comprises conjugating the protein to a polyethylene glycol (PEG).

8. The method of claim 7, wherein the PEG is a maleimide-PEG.

9. The method of claim 8, wherein the maleimide is linked to the PEG via an ethylene linker.

10. The method of claim 8, wherein the maleimide-PEG is conjugated to a thiol moiety of the protein selected from the group consisting of an intrinsic thiol moiety of a cysteine residue of the protein, a thiol moiety of a thiolated lysine residue of the protein, and a combination thereof, and the maleimide-PEG has the structure (VIII)

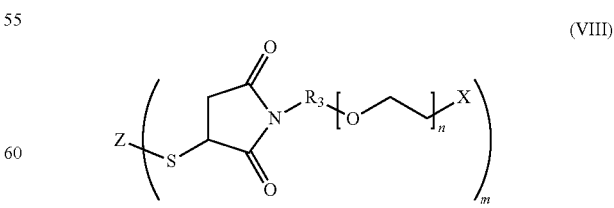

wherein
Z represents the protein,
S is a thiol of the protein,
$R_3$ is an alkylene or phenylene group, X is a terminal group, m is the average number of activated-PEG polymers conjugated to the protein, and n represents the average number of oxyethylene units of a PEG having an average molecular weight of about 2,000 to about 20,000 Daltons.

11. The method of claim 7, wherein the PEG is a succinimidyl valerate PEG (SVA-PEG).

12. The method of claim 1, wherein the hemoglobin tetramer is deoxygenated, liganded with CO, liganded with NO, or liganded with a mixture of CO and NO.

13. The method of claim 1, wherein the nitroxylating agent is present at about a 5-fold to about 100-fold molar excess over the protein.

14. The method of claim 1, wherein the reaction is carried out at a temperature of about 2° C. to about 30° C.

15. The method of claim 1, wherein the reaction is allowed to proceed for about three to about 20 hours.

16. The method of claim 1, wherein the reaction is carried out in an aqueous solvent.

17. The method of claim 1, wherein the reaction is carried out at a pH of about 6.5 to about 8.5.

18. The method of claim 12, wherein the hemoglobin tetramer is liganded with CO.

\* \* \* \* \*